US009877862B2

(12) United States Patent
Weadock et al.

(10) Patent No.: US 9,877,862 B2
(45) Date of Patent: Jan. 30, 2018

(54) TONGUE SUSPENSION SYSTEM WITH HYOID-EXTENDER FOR TREATING OBSTRUCTIVE SLEEP APNEA

(75) Inventors: Kevin S. Weadock, Hillsborough, NJ (US); Robert A. Rousseau, Ottsville, PA (US); David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 612 days.

(21) Appl. No.: 12/608,168

(22) Filed: Oct. 29, 2009

(65) Prior Publication Data
US 2011/0100377 A1    May 5, 2011

(51) Int. Cl.
*A61F 5/56*    (2006.01)

(52) U.S. Cl.
CPC .................... *A61F 5/566* (2013.01)

(58) Field of Classification Search
CPC .................... A61F 5/56; A61F 5/566
USPC ......... 128/848; 600/37; 623/23.72; 602/902; 433/140
See application file for complete search history.

(56) References Cited

U.S. PATENT DOCUMENTS

| 3,123,077 A | 3/1964 | Alcamo |
|---|---|---|
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |

(Continued)

FOREIGN PATENT DOCUMENTS

| CN | 2465680 | 12/2001 |
|---|---|---|
| CN | 201029957 | 3/2008 |

(Continued)

OTHER PUBLICATIONS

The Advance System, Aspire Medical, Inc., www.aspiremedical.com, 3 pp. (2008).

(Continued)

*Primary Examiner* — Ophelia A Hawthorne
*Assistant Examiner* — Caitlin Carreiro
(74) *Attorney, Agent, or Firm* — Doherty IP Law Group LLC

(57) ABSTRACT

A system for treating obstructive sleep apnea includes a first element implantable in a tongue and a second element implantable between muscle planes of an inframandibular region. The second element has a first end coupled with the first element and a second end coupled with a hyoid bone for preventing the base of the tongue from collapsing against an opposing pharyngeal wall during sleep. The first and second implantable elements have outer surfaces that are substantially impermeable to tissue in-growth to allow for post-surgical adjustment or removal, if necessary. The first implantable element is elongated and includes a first end, a second end, and a center section located between the first and second ends. The center section is implantable in the tongue, and the first and second ends of the first implantable element are advanceable beneath the tongue for being coupled with the anterior end of the second implantable element.

25 Claims, 13 Drawing Sheets

(56) References Cited

U.S. PATENT DOCUMENTS

| | | |
|---|---|---|
| 5,123,913 A | 6/1992 | Wilk et al. |
| 5,192,271 A | 3/1993 | Kalb et al. |
| 5,192,274 A | 3/1993 | Bierman |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 6/1998 | Scott et al. |
| 5,792,067 A | 8/1998 | Karell |
| 5,843,077 A | 12/1998 | Edwards |
| 5,931,855 A | 8/1999 | Buncke |
| 6,161,541 A | 12/2000 | Woodson |
| 6,190,401 B1 | 2/2001 | Green et al. |
| 6,241,747 B1 | 6/2001 | Ruff |
| 6,250,307 B1 | 6/2001 | Conrad et al. |
| 6,348,156 B1 | 2/2002 | Vishnoi et al. |
| 6,408,851 B1 | 6/2002 | Karell |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 8,307,831 B2 | 11/2012 | Rousseau |
| 8,413,661 B2 | 4/2013 | Rousseau et al. |
| 2001/0037133 A1 | 11/2001 | Knudson et al. |
| 2002/0144685 A1 | 10/2002 | Ivanovich et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0149488 A1 | 8/2003 | Metzger et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0044366 A1 | 3/2004 | Bonutti et al. |
| 2004/0102796 A1 | 5/2004 | Hill et al. |
| 2004/0153127 A1 | 5/2004 | Gordon et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1* | 9/2006 | Jackson ............ A61B 17/0401 128/860 |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102004 A1 | 5/2007 | Nelson et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0144539 A1 | 6/2007 | van der Burg et al. |
| 2007/0190108 A1 | 8/2007 | Datta et al. |
| 2007/0204866 A1* | 9/2007 | Conrad ................ A61F 2/00 128/848 |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0267027 A1 | 11/2007 | Nelson et al. |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1* | 2/2008 | Woodson ............ A61F 5/566 128/860 |
| 2008/0053461 A1* | 3/2008 | Hirotsuka et al. ........... 128/848 |
| 2008/0066764 A1 | 3/2008 | Paraschac et al. |
| 2008/0066765 A1 | 3/2008 | Paraschac et al. |
| 2008/0066767 A1* | 3/2008 | Paraschac ............ A61F 5/566 128/848 |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |

(56) References Cited

U.S. PATENT DOCUMENTS

| | | |
|---|---|---|
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau |
| 2010/0080791 A1 | 4/2010 | Rousseau |
| 2010/0106246 A1 | 4/2010 | Rousseau |
| 2010/0108077 A1 | 5/2010 | Lindh |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau |
| 2010/0234794 A1 | 9/2010 | Weadock |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | van der Burg et al. |
| 2012/0123449 A1 | 5/2012 | Schaller et al. |
| 2012/0160249 A1 | 6/2012 | Thomason et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 | 9/2011 |
| DE | 10245076 | 4/2004 |
| EP | 2145587 | 1/2010 |
| EP | 2386252 A1 | 11/2011 |
| EP | 2517633 | 10/2012 |
| FR | 2651113 | 3/1991 |
| JP | 2001145646 | 5/2001 |
| JP | 2003265621 | 9/2003 |
| RU | 2005447 | 1/1994 |
| RU | 2202313 | 4/2003 |
| SU | 927236 | 5/1982 |
| SU | 1697792 | 12/1991 |
| WO | 199713465 | 4/1997 |
| WO | 1999000058 | 1/1999 |
| WO | 2000066050 | 11/2000 |
| WO | 2001021107 | 3/2001 |
| WO | 2003096928 | 11/2003 |
| WO | 2004016196 | 2/2004 |
| WO | 2004020492 | 3/2004 |
| WO | 2004021869 | 3/2004 |
| WO | 2004021870 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2005122954 | 12/2005 |
| WO | 2006012188 | 2/2006 |
| WO | 2006072571 | 7/2006 |
| WO | 2006108145 | 10/2006 |
| WO | 2007056583 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2007295338 | 12/2007 |
| WO | 2008118913 | 10/2008 |
| WO | 2009023256 | 2/2009 |
| WO | 2009036094 | 3/2009 |
| WO | 2010019376 | 2/2010 |
| WO | 2010035303 | 4/2010 |
| WO | 2010065341 | 6/2010 |
| WO | 2012004758 | 1/2012 |
| WO | 2012041205 | 4/2012 |
| WO | 2012064902 | 5/2012 |
| WO | 2012170468 | 12/2012 |

OTHER PUBLICATIONS

The Pillar Procedure, Restore Medical, Inc., www.restoremedical.com, 2 pp. (2008).

Repose Genioglossus Advancement, INFLUENT Medical, www.influ.ent.com, 1 page. (2008).

Vicente et al., "Tongue-Base Suspension in Conjunction with Uvulopapatopharyngoplasty for Treatment of Severe Obstructive Sleep Apnea: Long-Term Follow-Up Results", The Laryngoscope, vol. 116(7), pp. 1223-1227 (2006).

Cole et al., "Snoring: A Review and a Reassessment", J. of Otolaryngology, pp. 303-306 (1995).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolaryngology, vol. 17, No. 4, Dec. 2006, pp. 252-256.

Schwab et al., "Upper airway and soft tissue changes induced by CPAP in normal subject", Am. J. Respit. Crit. Care Med., vol. 154, No. 4, Oct. 1996, pp. 1106-1116.

Schwartz et al., "Effects of electrical stimulation to the soft palate on snoring and obstructive sleep apnea", J. Prosthetic Dentistry, pp. 273-281 (1986).

Shamsuzzaman et al., "Obstructive Sleep Apnea; Implications for Cardiac and Vascular Disease", JAMA vol. 290 (14); pp. 1906-1914.

Teles et al., "Use of Palatal Lift Prosthesis on Patient Submitted to Maxillectomy: A Case Report", Applied Cancer Res. 2005, vol. 25(3), pp. 151-154.

Harries et al., "The Surgical treatment of snoring", J. of Laryngology and Otology., pp. 1105-1106 (1996).

Wassmuth et al., "Cautery-assisted palatal stiffening operation for the treatment of obstructive sleep apnea syndrome", Otolaryngology—Head and Neck Surgery, vol. 123(1), pp. 55-60 (Jul. 2000).

Wiltfang et al., "First results on daytime submandibular electrostimulation of suprahyoidal muscles to prevent night-time hypopharyngeal collapse in obstructive sleep apnea syndrom", Intl J. of Oral & Maxillofacial Surgery, pp. 21-25 (1999).

Notification of Transmittal of the International Search Report and the Written Opinion of the International Search Authority or the Declaration dated Feb. 3, 2010; PCT/US2009/051921; International Filing Date: Jul. 28, 2009.

Notification of Transmittal of the International Search Report and the Written Opinion of the International Search Authority or the Declaration dated May 25, 2010; PCT/US2010/023152; International Filing Date: Apr. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

(56) References Cited

OTHER PUBLICATIONS

International Search Report dated Apr. 29, 2010 for International Patent Application No. PCT/US2009/065293.

International Search Report dated May 25, 2010 for International Patent Application No. PCT/US2010/025778.

Database WPI Week 198312, Thomson Scientific, London, GB; AN 1983-D9513K XP002693421, -& SU 927 236 A1 (Petrozazodsk Univ) May 15, 1982 (May 15, 1982) abstract (see figures 7 & 8).

International Search Report dated May 25, 2010 for International Patent Application No. PCT/US2010/023152.

International Search Report dated Apr. 9, 2013 for International Patent Application No. PCT/US2012/061569.

International Search Report dated Apr. 2, 2013 for International Patent Application No. PCT/US2012/067708.

Written Opinion dated Nov. 27, 2012 for International Patent Application No. PCT/US2012/056577.

Schleef et al., "Cytokine Activation of Vascular Endothelium, Effects on Tissue—Type 1 Plasminogen Activator Inhibitor", The J. of Biological Chem., vol. 263, No. 12, pp. 5797-5803 (1988).

International Search Report dated Dec. 29, 2009 for International Patent Application No. PCT/US2009/061455.

International Search Report dated Jan. 21, 2010 for International Patent Application No. PCT/US2009/052110.

International Search Report dated Jan. 14, 2011 for International Patent Application No. PCT/US2010/052628.

International Search Report dated Jan. 20, 2011 for International Patent Application No. PCT/US2010/052644.

International Search Report dated Jan. 24, 2011 for International Patent Application No. PCT/US2010/052649.

International Search Report dated Feb. 28, 2011 for International Patent Application No. PCT/US2010/059673.

Medtronic AIRvance System for Obstructive Sleep Apnea, http://www.medtronic.com/for-healthcare-professionals/products-therapies/ear-nose-throat/sleep-disordered-breathing-, 2013, 3 pages.

International Search Report for International Application No. PCT/US2013/043238, dated Oct. 2, 2013, 7 pages.

\* cited by examiner

TONGUE SUSPENSION SYSTEM WITH HYOID-EXTENDER FOR TREATING OBSTRUCTIVE SLEEP APNEA

BACKGROUND OF THE INVENTION

Field of the Invention

The present invention generally relates to treating sleep disorders, and more specifically relates to implant systems, devices and methods for treating patients suffering from obstructive sleep apnea.

Description of the Related Art

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about two (2) cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal for stiffening the palate.

Surgical procedures such as those mentioned above continue to have problems. More specifically, the area of tissue that is surgically treated (e.g., removal of palatal tissue or scarring of palatal tissue) is often larger than is necessary to treat the patient's condition. In addition, the above-mentioned surgical procedures are often painful and have extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. The Pillar device has been associated with a number of adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" on the tongue, causing device failure and requiring subsequent removal.

In spite of the above advances, there remains a need for additional systems, devices and methods for treating OSA through minimally invasive approaches that provide long term results, that encourage patient compliance, and that minimize patient discomfort. More specifically, there remains a need for implant systems for treating obstructive sleep apnea that may be easily removed or adjusted post-surgery, if necessary. There also remains a need for implant systems and methods for treating obstructive sleep apnea that do not anchor to the mandible so as to avoid the risk to dentition associated with prior art mandibular anchor systems.

SUMMARY OF THE INVENTION

In one embodiment, a system for treating obstructive sleep apnea includes a hyoid extender and a tongue suspension element, both of which are substantially impermeable to tissue in-growth. In one embodiment, the tongue suspension element is undifferentiated along its length and is partially implanted near the base of the tongue. The tongue suspension element may include a biocompatible, flexible ribbon or a suture. The hyoid extender is preferably coupled to the hyoid bone and is implanted between two muscle planes located beneath the tongue. The lower end of the tongue suspension element is preferably secured to an anterior end of the hyoid extender. When implanted, the system desirably prevents the tongue base from sealing against the pharyngeal wall or soft palate during sleep so as to prevent obstruction of the airway. The hyoid-coupled anchor system of the present invention desirably overcomes limitations found in prior art devices because the risk to dentition associated with mandibular anchor systems is avoided. In addition, the system disclosed herein may be implanted during a single surgical procedure. Moreover, the system is preferably impermeable to tissue in-growth so as to enable a surgeon to adjust the degree to which the tongue is suspended during implantation and/or post-surgery. In one embodiment, the impermeability of the system components to tissue in-growth enables one or more of the components to be easily removed after implantation, if necessary, to remove or adjust the system.

In one embodiment, a system for treating obstructive sleep apnea preferably includes a first element implantable in a tongue, and a second element implantable between two muscle planes within an inframandibular region located beneath the tongue. The first implantable element may be flexible and may be an elongated ribbon or an elongated suture. In one embodiment, the second element may be positioned between the geniohyoid and mylohyoid muscles. The second element preferably has a first end adapted for being coupled with the first element and a second end adapted for being coupled with a hyoid bone for moving a posterior tongue surface away from an opposing pharyngeal wall. The first and second implantable elements desirably have outer surfaces that are impermeable to tissue in-growth, that are biocompatible, and that are non-resorbable.

In one embodiment, the first implantable element may be made of materials such as polytetrafluoroethylene, polyurethane, polyethylene, teraphthalate, and silicone, or a combination of two or more of the above-listed materials. The second implantable element may be made of materials such as e-PTFE, Teflon®, polypropylene, silicone, polyurethane, nitinol, stainless steel, polyethylene, terepthalate, and silk, or a combination of two or more of the above-listed materials.

In one embodiment, the first implantable element is preferably elongated. The first implantable element may include a first end, a second end, and a center section located between the first and second ends. In one embodiment, the center section of the first implantable element is implantable in the tongue. The first and second ends of the first implantable element are advanceable beneath the tongue for being secured to the first end of the second implantable element (i.e., the hyoid extender). Advancing elements such as needles, awls, or pins may be coupled to the first and second ends of the first implantable element for advancing the first and second ends through tissue.

In one embodiment, the central area of the first implantable element includes a buttress defining a larger width region of the first implantable element. In one embodiment, the buttress area has a greater width than the width of the first and second ends. In one embodiment, the first element is implantable in the tongue so that the buttress extends along an axis that traverses an anterior-posterior axis of the tongue. In one embodiment, the buttress area extends laterally in an oral cavity and substantially perpendicular to the anterior-posterior axis of the tongue.

In one embodiment, the first end of the second implantable element desirably has at least one anchor point for securing the lower end of the first implantable element or the first and second ends of the first implantable element to the second implantable element. The at least one anchor point may include one or more loops adapted to receive the first and second ends of the first implantable element.

In one embodiment, the second implantable element may include at least one pair of stabilizing arms that extend outwardly from an elongated shaft and that are implantable between two muscle planes located beneath the tongue for stabilizing the second implantable element. In one embodiment, the stabilizing arms may be placed between two muscle planes beneath the tongue such as beneath either the geniohyoid or digastric musculature. In one embodiment, the at least one pair of laterally extending stabilizing arms are preferably located adjacent the first end of the second implantable element. The second or posterior end of the second implantable element preferably includes at least one concave surface adapted to conform to and engage an anterior face of a hyoid bone. The second end of the second implantable element preferably includes a pair of spaced arms, whereby each of the spaced arms has a posterior end with a concave surface adapted to abut against, conform to, and/or engage the anterior face of a hyoid bone.

In one embodiment, a system for treating obstructive sleep apnea includes a first element having an upper end implanted in a tongue and a lower end extending beneath the tongue, and a second element implanted between muscle planes located beneath the tongue. The second element preferably has an anterior end coupled with the lower end of the first element and a posterior end coupled with a hyoid bone, whereby the first and second elements have outer surfaces that are impermeable to tissue in-growth. Although the present invention is not limited by any particular theory of operation, it has been observed that prior art OSA implants enable tissue in-growth all the way through the implant. As a result, the implant may not be removed and/or adjusted after surgery without the patient undergoing a rather intrusive surgical procedure. The substantially impermeable nature of the implant to cells that is disclosed herein enables post-operative adjustment and/or removal. Although preferred embodiments are substantially impermeable, it is contemplated that certain embodiments of the present invention may provide for limited tissue in-growth, i.e. not all the way through the implant.

In one embodiment, the upper end of the first element desirably includes at least one loop implanted in the tongue and the lower end of the first element includes at least one free end adapted for anchoring the first element with the second element. The at least one loop may be wrapped around a band of fibers found in the tongue.

In one embodiment, the anterior end of the second element desirably comprises an anchor point for anchoring the at least one free end of the first element with the anterior end of the second element. The posterior end of the second element preferably includes at least one concave surface adapted to engage an anterior face of the hyoid bone for coupling the second element with the hyoid bone.

In one embodiment, the second implantable element or hyoid extender preferably includes a plate having a top surface and a bottom surface, and at least one through-hole located adjacent an anterior end of the plate and extending from the top surface to the bottom surface of the plate. The at least one through-hole is adapted to receive at least one of the ends of the first element for anchoring the first element to the second element.

In one embodiment, the second implantable element may include a first section, a second section spaced from the first section, and at least one spring element coupling the first and second sections together for enabling the first and second sections to move toward and away from one another. For example, the second section may move away from the first section when a patient swallows, however, the at least one spring element will return the first and second sections to normal spacing after the patient completes the swallow. The second implantable element may include a first flexible film extending between and overlying respective top major surfaces of the first and second sections, and a second flexible film extending between and overlying respective bottom major surfaces of the first and second sections. In one embodiment, the first and second flexible films preferably cover the at least one spring element extending between the first and second sections so that the at least one spring element is covered by the films and is not exposed.

In one embodiment, a method for treating obstructive sleep apnea includes providing a tongue suspension element having an outer surface that is substantially impermeable to tissue in-growth, implanting at least a portion of the tongue suspension element in a tongue, and positioning a lower end of the tongue suspension element beneath the tongue. The method preferably includes providing a hyoid bone extender having an outer surface that is substantially impermeable to tissue in-growth, implanting the hyoid bone extender between muscle planes located beneath the tongue (e.g. within inframandibular musculature), and coupling the lower end of the tongue suspension element with an anterior end of the hyoid bone extender. The method preferably includes coupling a posterior end of the hyoid bone extender with a hyoid bone for moving a posterior surface of the tongue away from an opposing surface of a pharyngeal wall.

In one embodiment, the posterior end of the hyoid bone extender preferably comprises at least one concave surface, and the method preferably includes abutting the at least one concave surface at the posterior end of the hyoid bone extender against an anterior surface of the hyoid bone. The method may include anchoring the posterior end of the hyoid bone extender to the hyoid bone using sutures, clips, clamps, staples, barbs, or adhesive.

As used herein, the term "inframandibular musculature" generally refers to the geniohyoid, mylohyoid, digastric and pterygoid muscles. In one embodiment, tension is preferably applied to the first and second ends of the first implantable element, also referred to as a tongue suspension element, for pulling the center area of the first implantable element toward the inframandibular musculature, which, in turn, moves a posterior surface of the tongue away from an opposing surface of a pharyngeal wall. In one embodiment, after the tension is applied, the first and second ends of the first implantable element are desirably anchored to the anterior end of the second element implanted between two muscle planes within the inframandibular musculature for maintaining a space between the posterior surface of the tongue and the opposing surface of the pharyngeal wall during sleep.

In one embodiment, the first implantable element may include a first set of barbs projecting from the first end and a second set of barbs projecting from the second end. The first and second set of barbs may project away from one another in opposite directions. The barbs preferably grip the tongue tissue for preventing slippage of the tissue relative to the first implantable element.

In one embodiment, a method of treating obstructive sleep apnea may include wrapping at least a portion of the first implantable element (e.g., the tongue suspension element) around a bundle of muscle fibers extending through a tongue so as to form at least one loop around the bundle of fibers, compressing the bundle of fibers using the at least one loop, and coupling a tether or line with the loop. The method desirably includes advancing a free end of the tether toward inframandibular musculature, applying tension to the tether for pulling the looped elongated element toward the inframandibular musculature so as to move a posterior surface of the tongue away from an opposing surface of a pharyngeal wall, and anchoring the tether to a second element implanted within the inframandibular musculature and anchored to the hyoid bone. In one embodiment, the tether is integrally formed with the at least one loop.

These and other preferred embodiments of the present invention will be described in more detail below.

DETAILED DESCRIPTION

Figure 1:
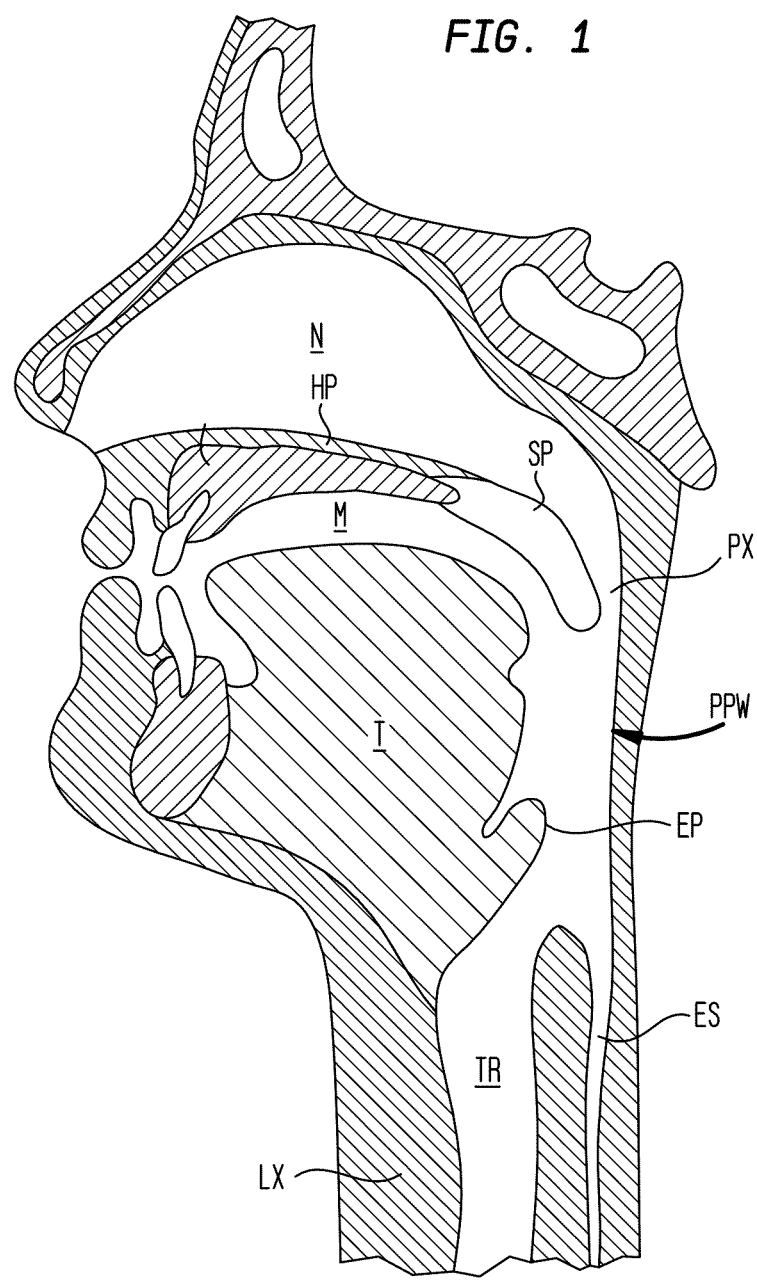
FIG. 1 shows a cross-sectional view of a human head including a nasal cavity and a pharynx.

FIG. 1 shows a cross-section of a human head with anatomical structures including the nasal cavity N, the hard palate HP, the soft palate SP, the mouth M, the tongue T, the trachea TR, the epiglottis EP, the esophagus ES, and the posterior pharyngeal wall PPW.

Figure 2:
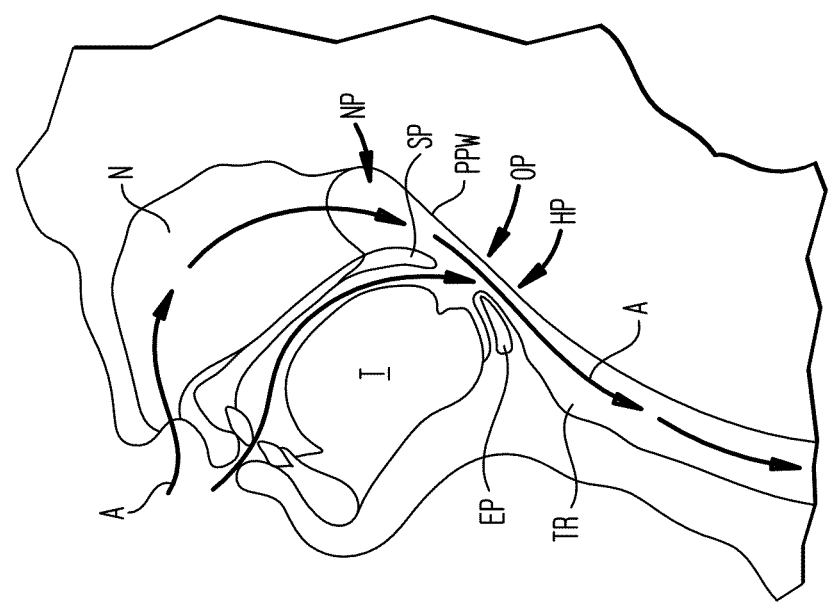
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP.

The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles of the body relax during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly referred to as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are diagnosed as having obstructive sleep apnea syndrome. As the airway is obstructed, the individual makes repeated attempts to inhale. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Figure 3:
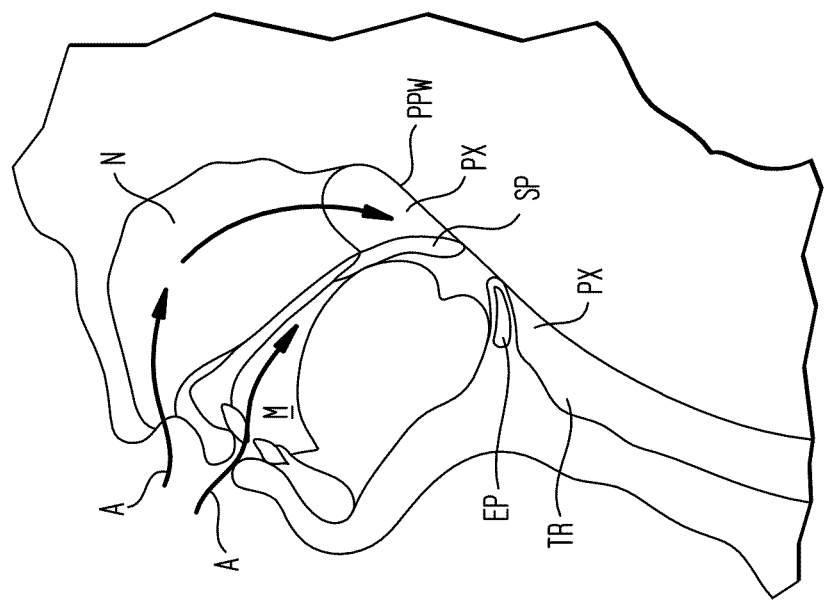
FIG. 3 shows a cross-sectional view of the nasal cavity and the pharynx of a human during an obstructive sleep apnea episode.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible. Referring to FIG. 3, without normal muscle tone to keep their shape and to keep them in place either alone or as a group, the posterior surface of the tongue T, the epiglottis EP, or soft palate SP may collapse and block the airway A. The present invention provides systems, methods and devices for avoiding these problems.

Figure 4A:
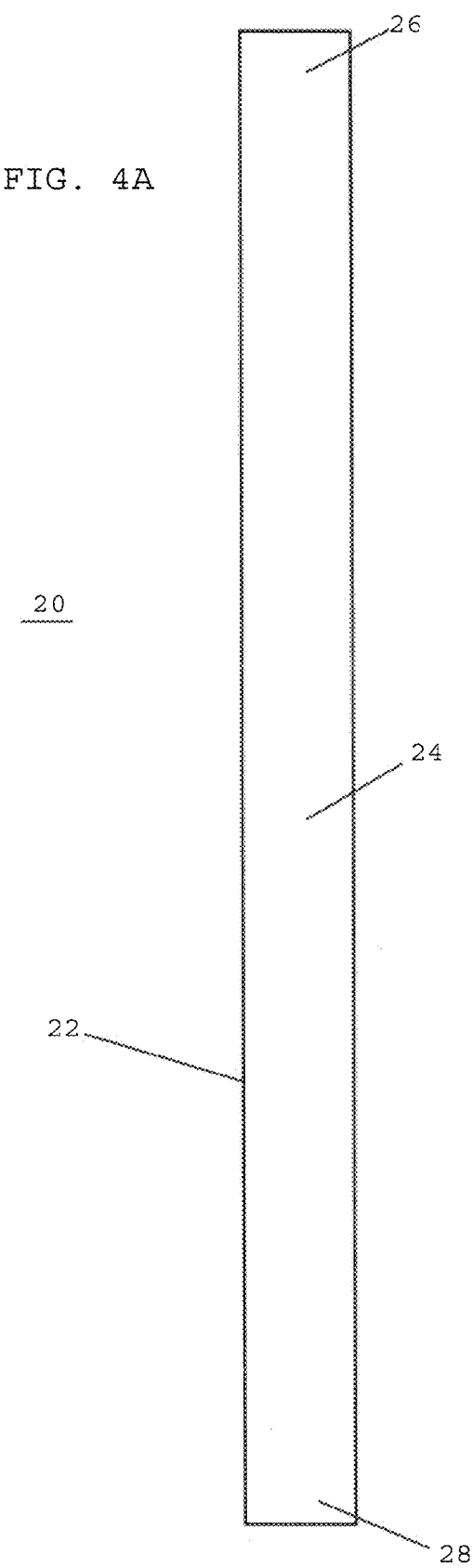
FIGS. 4A and 4B show a tongue suspension element for a system for treating obstructive sleep apnea, in accordance with one embodiment of the present invention.
Figure 4B:
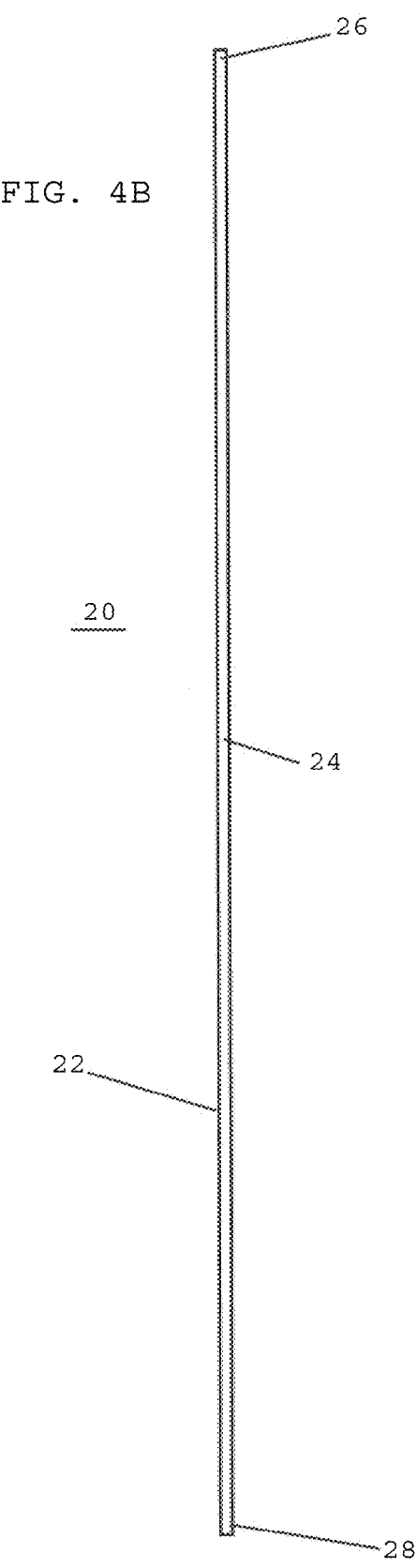

Referring to FIGS. 4A and 4B, in one embodiment, a system for treating obstructive sleep apnea includes a first implantable element or tongue suspension element 20. The tongue suspension element 20 desirably includes an elongated member 22 having a center section 24, a first end 26 and a second end 28. The elongated member 22 is preferably flexible, and the first and second ends 26, 28 are preferably free ends. The tongue suspension member is desirably flexible and has a level of compliance that is approximately equal to that of the tongue. The tongue suspension element 20 is preferably biocompatible and may be a ribbon-like material such as an expanded Teflon material (e-PTFE). In one embodiment, the tongue suspension element 20 may include a biocompatible suture, which may or may not have barbs. Although not shown, needles or pins may be attached to the first and second ends 26, 28 for advancing the first and second ends through tissue.

In one embodiment, the tongue suspension element is substantially impermeable to tissue in-growth. In one embodiment, the tongue suspension element has an outer surface that limits tissue in-growth. In one embodiment, if tissue in-growth does occur, the tissue in-growth desirably penetrates the surface of the tongue suspension element by less than 500 microns. The tongue suspension element is preferably made of a biocompatible, non-resorbable, tissue growth impermeable material such as e-PTFE, Teflon, polypropylene, silicone, polyurethane, nitinol, stainless steel, polyethylene, terephalate, silk or other biocompatible non-resorbable materials well-known to those skilled in the art. The free ends of the tongue suspension members are desirably attached to a second implant element or hyoid extender coupled to a hyoid bone using knots, clips, glue, welds, or other well-known connecting elements.

In one embodiment, the tongue suspension element is undifferentiated along its length, i.e., there is no difference in structure, dimension, or composition along its entire length. In one embodiment, the tongue suspension element may have a central buttress having a width that is greater than the width of the first and second ends thereof. In one embodiment, the tongue suspension element 20 may incorporate one or more of the features (e.g. a buttress, a loop) disclosed in commonly assigned U.S. patent application Ser. No. 12/261,102, the disclosure of which is hereby incorporated by reference herein.

The hyoid extender is preferably made of a biocompatible, non-resorbable biomaterial such as e-PTFE, Teflon, polypropylene, polycarbonate, silicone, polyurethane, nitinol, stainless steel, polyethylene, terepthalate, silk or other biocompatible non-resorbable materials known to those skilled in the art of biomaterials. In one embodiment, the posterior end of the hyoid extender is desirably attached to or abutted against the hyoid bone during implantation. In one embodiment, the hyoid extender may be sutured to the hyoid bone. As noted above, the implantable components of the system disclosed herein, i.e., the tongue suspension element and the hyoid extender are preferably resistant to tissue in-growth. The term "substantially impermeable" means that, while tissue may attach to the surface of these elements, the tissue in-growth is generally easy to remove, if necessary, so that medical personnel may adjust and/or remove the system. The hyoid extender preferably allows for tongue suspension for treating OSA without the concerns that mandibular-based systems have for damaging nerves and the teeth they innervate.

Figure 5:
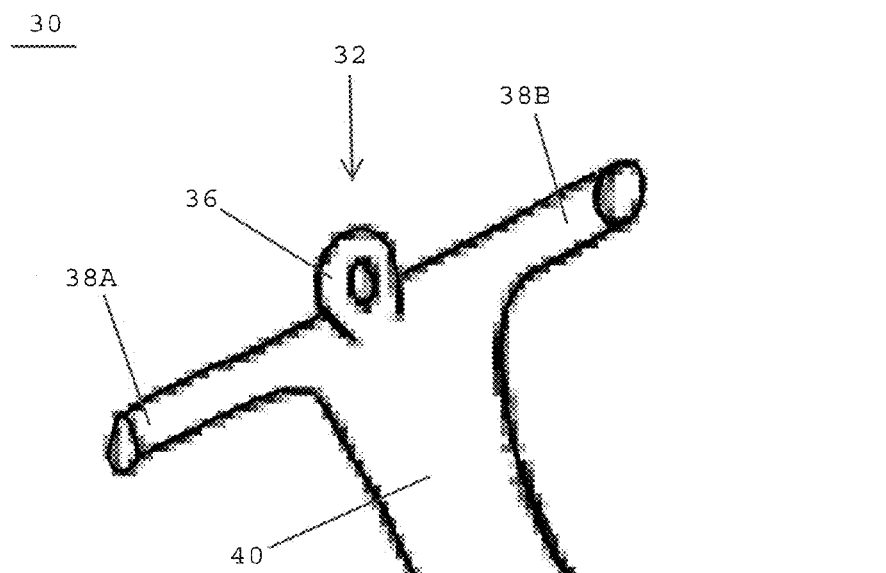
FIG. 5 shows a hyoid extender for a system for treating obstructive sleep apnea, in accordance with one embodiment of the present invention.

Referring to FIG. 5, in one embodiment, a system for treating obstructive sleep apnea includes a second implantable element or hyoid extender 30 having an anterior end 32 and a posterior end 34. In one embodiment, the hyoid extender 30 has an anterior loop 36 adapted to receive the free ends of the tongue suspension element shown and described above in FIGS. 4A and 4B. The anterior loop 36 may receive one or more of the first and second ends of the tongue suspension element for connecting the tongue suspension element to the hyoid extender. The hyoid extender 30 also desirably includes a pair of stabilizing arms 38A, 38B that extend away from one another along the anterior end 32 of the anchoring element 30. The hyoid extender 30 also desirably includes an elongated shaft 40 that extends between the anterior end 32 and the posterior end 34 thereof. In one embodiment, the elongated shaft 40 is split adjacent the posterior end 34 of the hyoid extender to define a first arm 42A and a second arm 42B. The posterior ends of the first and second arms 42A, 42B preferably include hyoid bone abutting elements 44A, 44B adapted to abut and engage a hyoid bone. In the particular embodiment shown in FIG. 5, the hyoid bone abutting elements 44A, 44B include concave surfaces 46A, 46B adapted to abut and engage an anterior surface of a hyoid bone.

Although the present invention is not limited by any particular theory of operation, it is believed that the anterior face of a typical hyoid bone has a convex curve so that the concave surfaces 46A, 46B at the posterior end of the hyoid extender 30 will preferably facilitate anchoring of the hyoid extender to the hyoid bone.

The hyoid extender is preferably made of a biocompatible, non-resorbable biomaterial such as e-PTFE, Teflon, polypropylene, silicone, polyurethane, nitinol, stainless steel, polyethylene terepthalate, silk or other biocompatible non-resorbable materials known to those skilled in the art of biomaterials. In one embodiment, the posterior end of the hyoid extender is desirably attached to or abutted against the hyoid bone during implantation. In one embodiment, the hyoid extender may be sutured to the hyoid bone. As noted above, the implantable components of the system disclosed herein, i.e., the tongue suspension element and the hyoid extender are preferably resistant to tissue in-growth. While tissue may attach to the surface of these elements, the tissue in-growth is generally easy to remove, if necessary, so that medical personnel may adjust and/or remove the system. The hyoid extender preferably allows for tongue suspension for treating OSA without the concerns that mandibular-based systems have for damaging nerves and the teeth they innervate.

Figure 6:
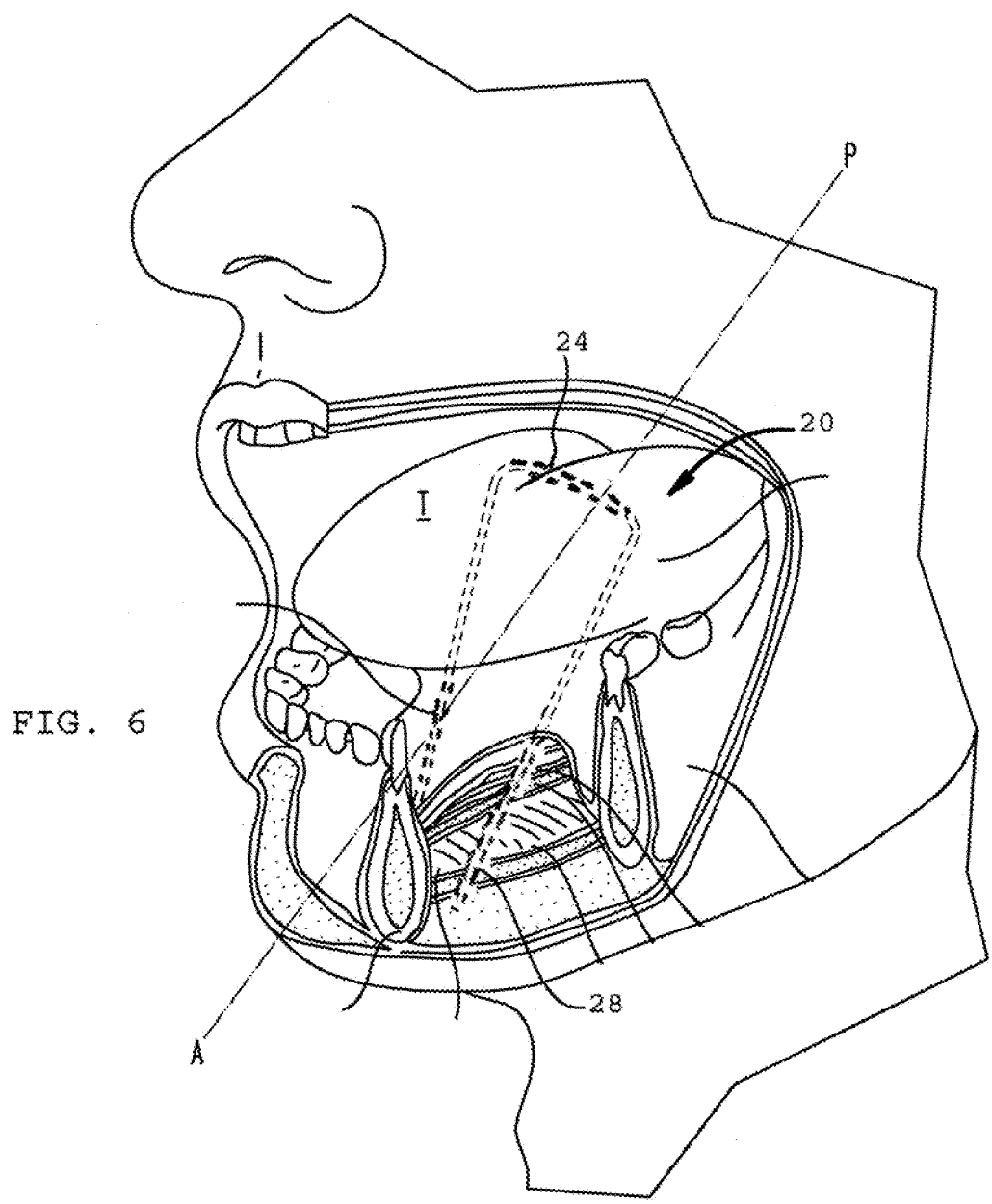
FIG. 6 shows a cross-sectional view of a human head including a nasal cavity after implantation of the tongue suspension element shown in FIGS. 4A and 4B, in accordance with one embodiment of the present invention.

Referring to FIG. 6, in one embodiment, the tongue suspension element 20 shown in FIGS. 4A and 4B may be implanted within the oral cavity of a patient. As shown in FIG. 6, an oral cavity typically includes a tongue T, a mylohyoid muscle, a geniohyoid muscle, and a genioglossus muscle. The mylohyoid muscle has an anterior end anchored to a mandible and a posterior end anchored to a hyoid bone (not shown). In the particular embodiment shown in FIG. 6, the tongue suspension element 20 is preferably positioned within the tongue so that the center section 24 of the tongue suspension element is located in the center portion of the base of the tongue and extends laterally toward the sides of the oral cavity. In one embodiment, the center section 24 of the tongue suspension element desirably extends along an axis that traverses or is substantially perpendicular to an anterior-posterior axis of the tongue T (designated A-P). In one embodiment, the center section 24 of the tongue suspension element 20 may have a larger surface area or buttress for holding the implant in place so as to avoid the "cheese cutter" effect that typically occurs when using prior art devices. In one embodiment, after the center section 24 is implanted, the first and second ends 26, 28 of the tongue suspension element 20 are desirably advanced into the inframandibular region. In one embodiment, the first end 26 of the tongue suspension element 20 preferably extends from the center section 24 toward the anterior end of the mylohyoid muscle, and the second end 28 of the tongue suspension element 20 desirably extends from the center section 24 toward the anterior end of the mylohyoid muscle.

Figure 7:
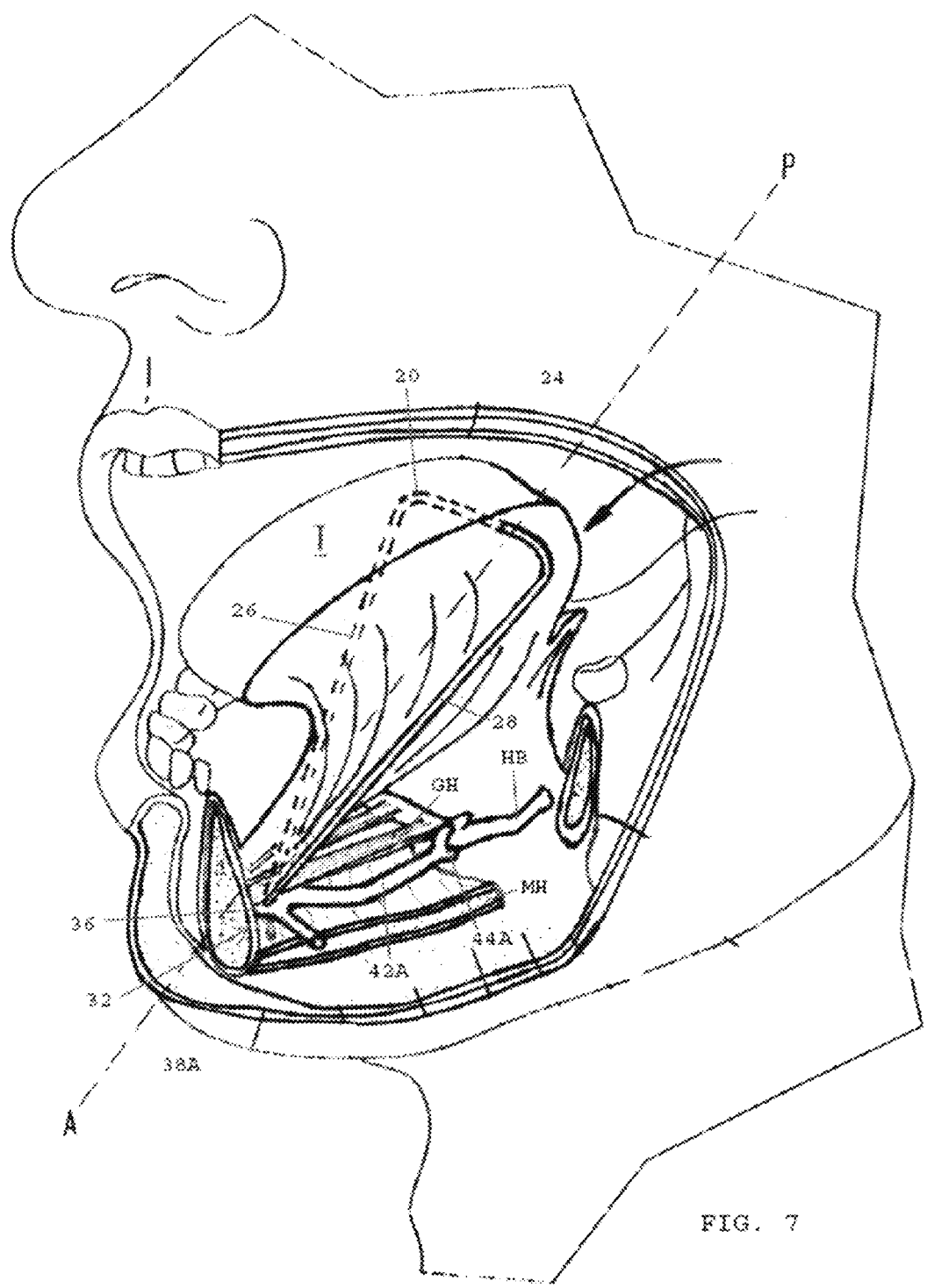
FIG. 7 shows a view of a human tongue, mandible, and hyoid bone after implantation of the tongue suspension element of FIGS. 4A and 4B and the hyoid extender of FIG. 5, in accordance with one embodiment of the present invention.

FIG. 7 shows the implanted tongue suspension element 20 of FIGS. 4A-4B and the hyoid extender 30 of FIG. 5. The tongue suspension element 20 preferably includes the center section 24 implanted in the patient's tongue T and the first and second free ends 26, 28 extending through the tissue of the tongue toward the anterior end of the geniohyoid muscles. The hyoid extender 30 is desirably implanted between two planes of the inframandibular musculature. In one embodiment, the free ends 26, 28 of the tongue suspension element 20 are preferably passed through the anterior loop 36 provided at the anterior end 32 of the hyoid extender 30. The two split arms 42A, 42B desirably slide between a muscle plane and have posterior ends 44A, 44B that engage an anterior face of the hyoid bone HB. Thus, the hyoid extender 30 desirably anchors the first and second ends 26, 28 of the tongue suspension element 20 to the hyoid bone HB (via the hyoid bone extender 30) so as to shift a posterior surface of the tongue T away from an opposing pharyngeal wall (not shown).

Referring to FIGS. 5 and 7, in one embodiment, the hyoid extender 30 desirably includes first and second laterally extending stabilizing arms 38A, 38B that stabilize the hyoid extender within a muscle plane. In one embodiment, the first and second stabilizing arms 38A, 38B may be placed in various locations including between two muscle planes beneath the tongue or beneath either the geniohyoid or digastrics musculature. In one embodiment, either the geniohyoid and/or the digastrics musculature have two separate bands that may be dissected from one another during implantation.

Referring to FIG. 7, in one embodiment, the hyoid bone engaging elements 44A, 44B at the posterior end of the hyoid extender 30 may be at least partially wrapped around the anterior face of the hyoid bone. In one particular embodiment, the hyoid bone engaging elements are wrapped around at least one-third or more of the circumference of the anterior face of the hyoid bone HB. The concave surfaces 46A, 46B at the posterior ends of the first and second arms 42A, 42B may be hooked at the point where the digastrics or geniohyoid muscles attach to the hyoid bone HB. In one embodiment, the concave surfaces 46A, 46B are preferably hooked to the fibrous tunnel on the hyoid bone that engages the mid-line of the digastrics muscle.

The implant system disclosed herein is preferably easily implanted while requiring only small incisions. In one embodiment, the hyoid extender is preferably implanted after the tongue suspension element is implanted. While the hyoid extender may be flat, in one or more embodiments, the hyoid extenders may be slightly bent in the middle to account for angles present in the mylohyoid muscle and to conform to the natural curvature of the mylohyoid and other muscles. The tongue suspension element may be implanted using one or more of the methods disclosed by Vicente et al. (Tongue-Base Suspension in Conjunction with Uvulopalatopharyngoplasty for Treatment of Severe Obstructive Sleep Apnea: Long-Term Follow-Up Results; The Laryngoscope, 116(7): 1223-1227). Applicants note, however, that Vincete et al. teach attachment of an implant to the mandible and, in contrast, the present invention teaches that the tongue suspension element is attached to the hyoid extender.

In one embodiment, a patient is prepared for surgery using local or general anesthesia. The first end of the tongue suspension element is advanced in a lateral direction through the posterior portion of the tongue until the center section of the tongue suspension element is centered in the tongue. A needle may be provided at the end of the first end and is preferably passed within the tongue from the posterior portion of the tongue through a generally anterior and inferior direction to engage the inframandibular musculature. The needle facilitates advancement of the first end through the tissue of the tongue T. The second end of the tongue suspension element is also preferably advanced through the tissue of the tongue in a similar manner.

In one embodiment, a small diameter trocar may be advanced through the floor of the mouth near the base of the tongue. A snare is preferably introduced through the lumen of the trocar to grab each of the first and second ends of the tongue suspension element. The first and second ends are preferably pulled through the trocar and the trocar is removed. A surgeon may pull the first and second ends of the tongue suspension element until the posterior surface of the tongue is advanced in an anterior direction so that it is unlikely to form a seal against the back wall of the pharynx during sleep. The first and second ends of the tongue suspension element may be attached to hyoid extender implanted within the inframandibular region to set the tongue in the new position. The first and second ends of the tongue suspension element may be attached to the hyoid extender using barbs, glue, sutures, clips, or any combination thereof, or by pulling the two ends of the tongue suspension element through the holes in the hyoid extender and knotting them together.

Figure 8:
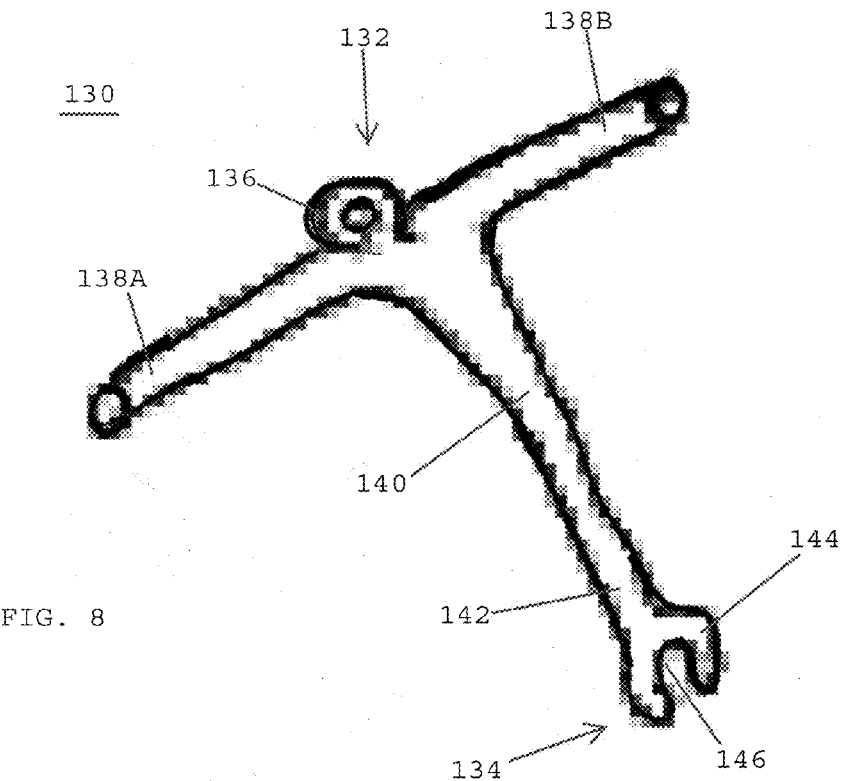
FIG. 8 shows a hyoid extender, in accordance with one embodiment of the present invention.

In other embodiments, hyoid extenders having different designs may be used in place of the hyoid extender shown in FIGS. 5 and 7. For example, referring to FIG. 8, in one embodiment, a hyoid extender 130 has an anterior end 132 and a posterior end 134. The anterior end 132 of the hyoid extender includes an anterior loop 136 and a pair of opposing stabilizing arms 138A, 138B for desirably stabilizing the anchoring element 130 between muscle planes. The hyoid extender 130 also includes an elongated shaft 140 that extends between the anterior and posterior ends 132, 134, respectively. The elongated shaft 140 includes a hyoid bone anchoring arm 142 that extends toward the posterior end 134 of the hyoid extender. The anchoring arm 142 includes a hyoid bone anchoring end 144 having a concave surface 146 adapted to abut against and engage the anterior face of the hyoid bone. As noted above, the first and second stabilizing arms 138A, 138B desirably extend between the planes of inframandibular musculature for stabilizing the hyoid extender between the planes of the musculature.

Figure 9:
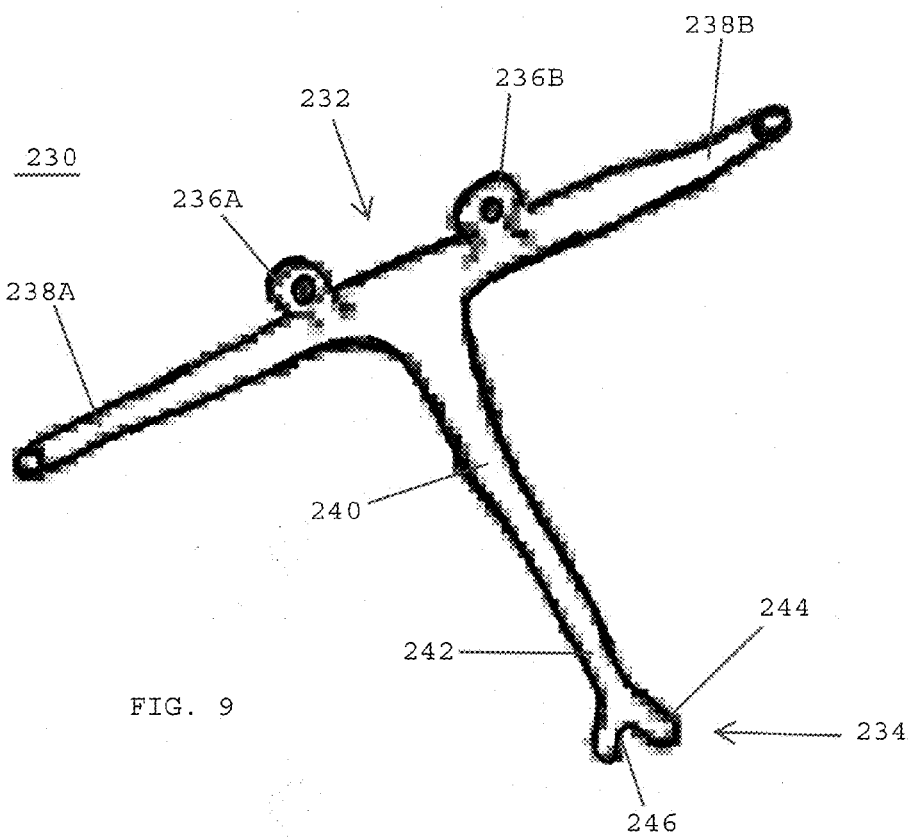
FIG. 9 shows a hyoid extender, in accordance with another embodiment of the present invention.

Referring to FIG. 9, in one embodiment, a hyoid extender 230 preferably has an anterior end 232 and an opposite posterior end 234. The anterior end 232 includes a pair of anterior loops 236A, 236B preferably adapted to receive the first and second ends of a tongue suspension element, such as the tongue suspension element shown and described above in FIGS. 4A and 4B. The hyoid extender 230 also desirably includes a pair of opposing stabilizing arms 238A, 238B that preferably extend in lateral directions adjacent the anterior end 232 of the hyoid extender 230. The anchoring element 230 also desirably includes an elongated shaft 240 that extends between the anterior and posterior ends thereof. The elongated shaft 240 desirably includes an anchoring arm 242 adjacent the posterior end that extends to the posterior end 234 of the hyoid extender. The posterior end of the anchoring arm 242 desirably includes a hyoid bone engaging element 244 including a concave surface 246 adapted to abut against and/or engage a hyoid bone.

Figure 10:
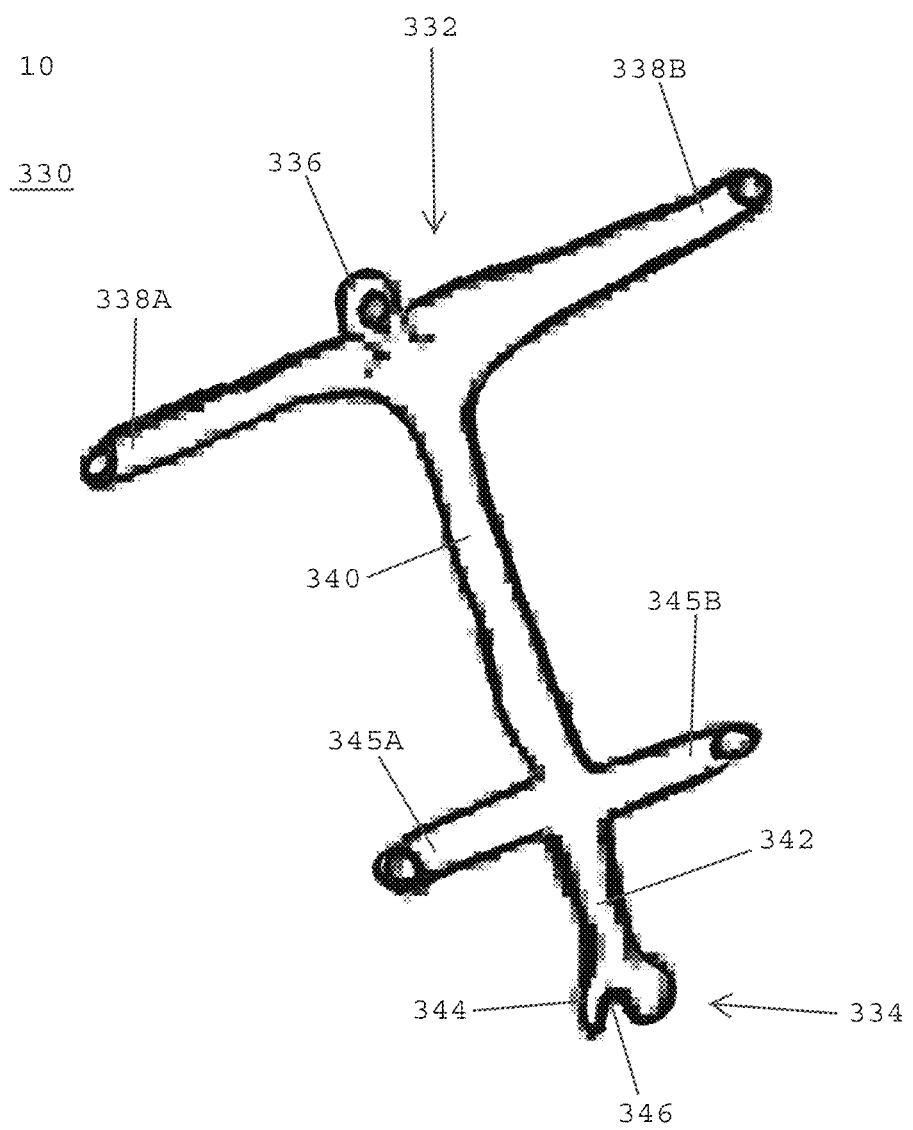
FIG. 10 shows a hyoid extender, in accordance with yet another embodiment of the present invention.

Referring to FIG. 10, in one embodiment, a hyoid extender 330 desirably has an anterior end 332 and an opposite posterior end 334. The hyoid extender 330 desirably includes an anterior loop 336 adjacent the anterior end 332 thereof. The hyoid extender 330 desirably includes a first pair of laterally extending stabilizing arms 338A, 338B. The first pair of laterally extending stabilizing arms 338A, 338B preferably extend along the anterior end 332 of the hyoid extender.

The hyoid extender 330 also desirably includes an elongated shaft 340 that extends between the anterior and posterior ends 332, 334 thereof. The elongated shaft 340 has a posterior end with an anchoring arm 342. The posterior end of the anchoring arm includes an anchoring element 344 having a concave surface 346 adapted to engage a hyoid bone, such as an anterior face of a hyoid bone. The hyoid extender 330 also desirably includes a second pair of supplemental stabilizing arms 345A, 345B that extend laterally from opposite sides of the elongated shaft 340. In one embodiment, the supplemental stabilizing arms 345A, 345B are located on the anchoring arm 342 and are closer to the posterior end 334 of the anchoring element than the anterior end 332 of the anchoring element. The first and second pairs of stabilizing arms desirably extend between the planes of the musculature within the inframandibular regions so as to stabilize the hyoid extender 330 and prevent the hyoid extender from shifting within the musculature.

Figure 11A:
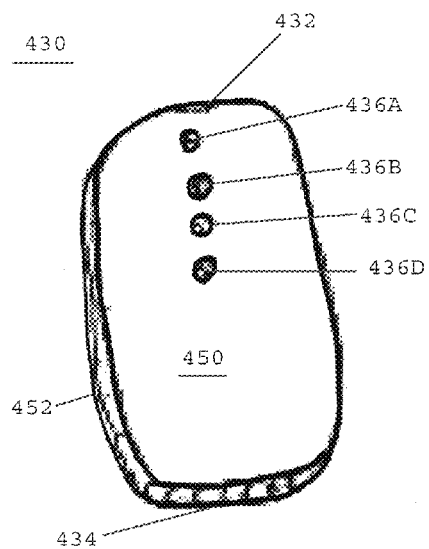
FIGS. 11A and 11B show a hyoid extender, in accordance with another embodiment of the present invention.
Figure 11B:
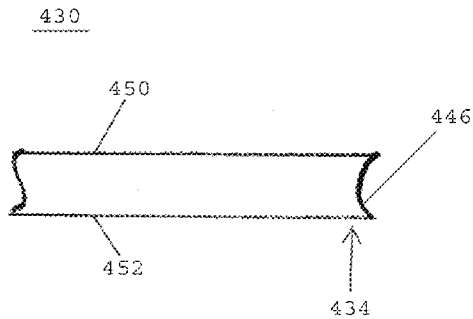

Referring to FIGS. 11A and 11B, in one embodiment, a hyoid extender 430 is a disc or plate including an anterior end 432 and a posterior end 434. The disc-shaped hyoid extender 430 desirably includes a series of through holes 436A-436D that enable a surgeon to select one of the holes for attaching the free ends of a tongue suspension element thereto so as to adjust for different sized patients and different surgical requirements. In one embodiment, the series of through holes 436A-436D are spaced at different distances from the anterior end 432 of the hyoid extender 430 to allow a surgeon to modify a procedure based upon patient anatomy or surgical requirements. For example, a surgeon may choose one of the through holes 436A-436D based upon how far the back of the tongue must be spaced from the opposing pharyngeal wall. Alternatively, the surgeon may wish to provide a certain angle between the tongue suspension element and the hyoid extender.

Referring to FIGS. 11A and 11B, the hyoid extender 430 desirably includes a first major surface 450 extending along the top of the hyoid extender and a second major surface 452 extending along the bottom of the hyoid extender. The posterior end 434 of the hyoid extender preferably includes a concave surface 446 adapted to engage a face (e.g. a convex face) of a hyoid bone, such as an anterior face of a hyoid bone. The concave surface 446 preferably extends along the posterior end 434 and between the top and bottom major surfaces 450, 452.

Figure 12A:
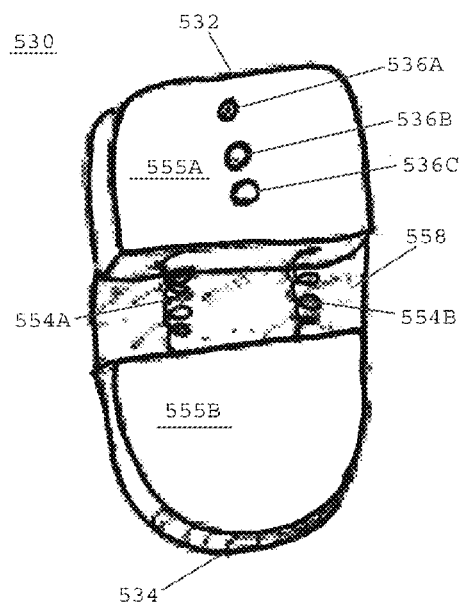
FIGS. 12A and 12B show a hyoid extender, in accordance with one embodiment of the present invention.
Figure 12B:
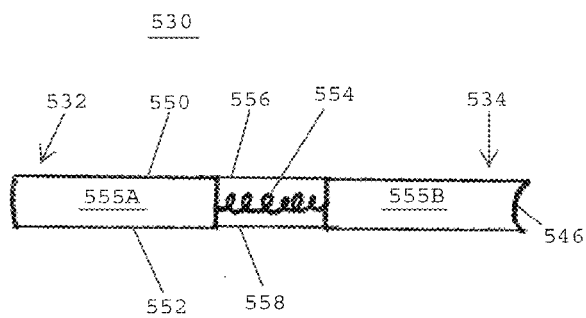

Referring to FIGS. 12A and 12B, in one embodiment, a hyoid extender 530 has a plate-like shaped appearance and includes an anterior end 532 and a posterior end 534. The hyoid extender 530 includes a series of through holes 536A-536C extending between a top major surface 550 and a bottom major surface 552 thereof. Each of the openings 536A-536C has a different spacing from the anterior end 532 of the anchoring element 530 for accommodating different surgical needs. The hyoid extender 530 also desirably includes one or more spring or flexible elements 554A, 554B that extend between first and second sections 555A, 555B of the hyoid extender. The spring elements 554A, 554B enable the first and second sections 555A, 555B to flex and/or move relative to one another such as may occur when a patient swallows. The hyoid extender 530 also desirably includes a biocompatible top film 556 and a biocompatible bottom film 558 that extend between the respective first and second sections 555A, 555B and that cover the respective upper and lower areas of the spring element 554A, 554B. The thin biocompatible films 556A, 558B desirably include biocompatible polymers such as polytetrafluoroethylene, polypropylene, polyurethane, silicone, and/or polyethylene.

Figure 13:
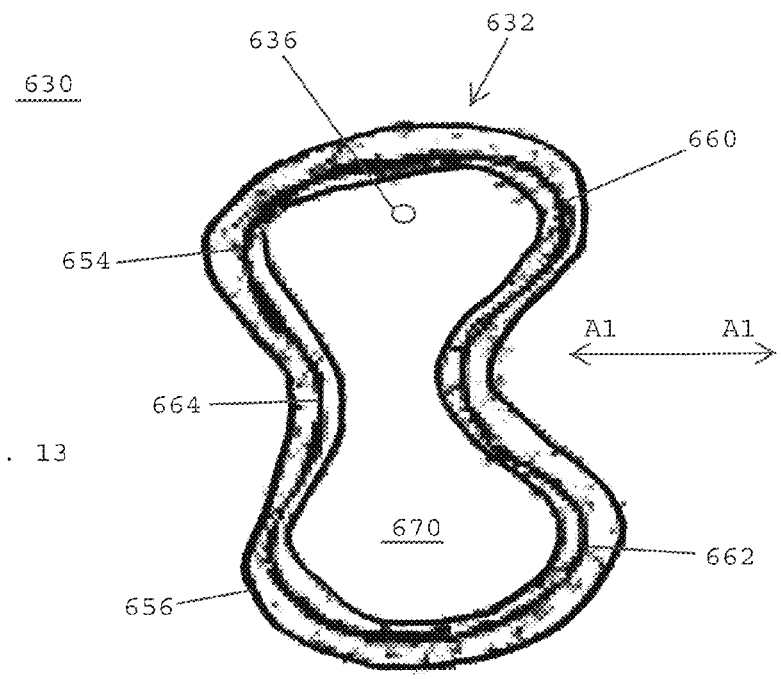
FIG. 13 shows a hyoid extender, in accordance with one embodiment of the present invention.

Referring to FIG. 13, in one embodiment, a hyoid extender 630 has an anterior end 632 and a posterior end 634. The hyoid extender 630 desirably includes a spring member 654 covered by a biocompatible, flexible film 656. In one embodiment, the spring member 654 has a shape that is similar in appearance to the number eight with a first loop 660 adjacent the anterior end 632 and a second loop 662 adjacent the posterior end 634. The spring member 654 also includes a central waist section 664 that extends between the first loop 660 and the second loop 662. The waist section 664 is normally in the position shown in FIG. 13. As the spring member 654 flexes (e.g. in response to a patient swallowing or speaking), the waist section 664 will spring inwardly or outwardly in the directions shown by the arrows designated $A_1$-$A_1$. After the external force is removed, the spring member 654 will preferably return to the shape shown in FIG. 13.

Referring to FIG. 13, in one embodiment, the hyoid extender 630 includes a first opening 636 extending through the width of the hyoid extender, which is located adjacent the anterior end 632 thereof. The first hole 632 is adapted to receive the lower end or the first and second free ends of a tongue suspension element, as shown and described herein. The posterior end 634 of the hyoid extender 630 may include a concave surface adapted to abut against and engage an anterior face of a hyoid bone for connecting the hyoid extender with the hyoid bone.

In one embodiment, the spring member 654 shown in FIG. 13 may be completely covered by a flexible biocompatible film that extends over the central area 670 of the spring member. In one embodiment, a first layer of film may extend over the top of the spring member 654 and a second layer of film may extend below bottom of the spring member 654. In one embodiment, the first and second layers of film preferably completely cover a central area 670 bounded by the spring member 654. The biocompatible film is preferably impermeable to tissue in-growth.

Figure 14:
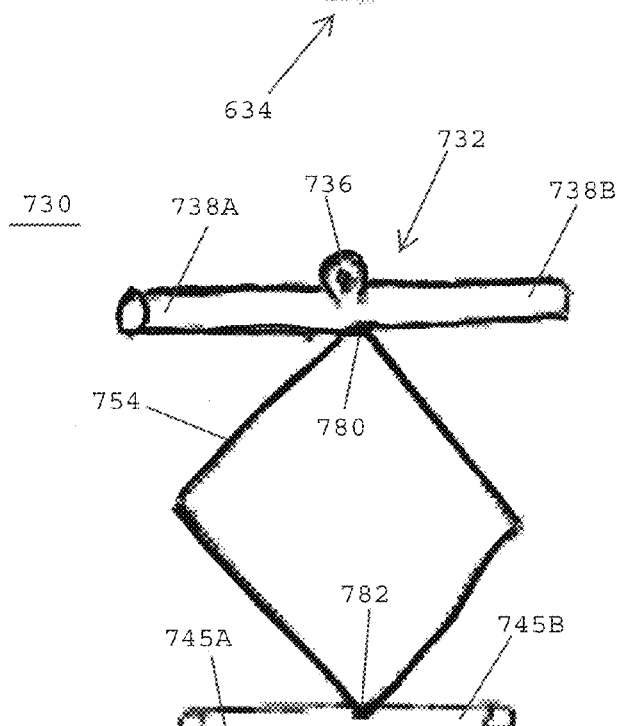
FIG. 14 shows a hyoid extender, in accordance with one embodiment of the present invention.

Referring to FIG. 14, in one embodiment, a hyoid extender 730 has an anterior end 732 and a posterior end 734. The anterior end 732 of the hyoid extender desirably includes an anterior anchoring loop 736 adapted to receive the free ends of a tongue suspension element. In one embodiment, instead of the anterior anchoring loop, holes can be drilled all the way through the thickness of the hyoid extender so that one or both ends of the tongue suspension element can be passed through and knotted or stapled together. The anterior end 732 also desirably includes a first pair laterally extending stabilizing arms 738A, 738B that extend along the anterior edge of the anchoring element 730. The hyoid extender 730 also desirably includes a second pair of stabilizing arms 745A, 745B that extend adjacent the posterior end 734 of the anchoring element 730. The posterior end 734 of the anchoring element also desirably includes a hyoid extender 744 having a concave surface 746 adapted to engage an anterior face of a hyoid bone. A spring member 754 desirably has a first end 780 connected to the first pair of stabilizing arms 738A, 738B and a second end 782 connected to the second pair of stabilizing arms 745A, 745B. The spring member 754 desirably enables the first and second pairs of stabilizing arms to move toward and away from one another. Although not shown, one or more flexible biocompatible films may extend between the first and second sets of stabilizing arms for covering the spring member 754.

Figure 15A:
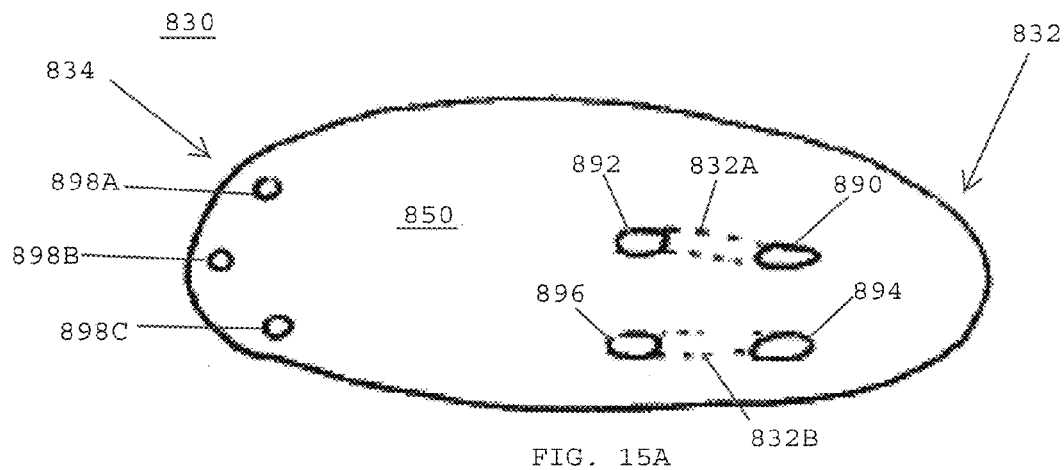
FIG. 15A shows a top plan view of a hyoid extender, in accordance with one embodiment of the present invention.
Figure 15B:
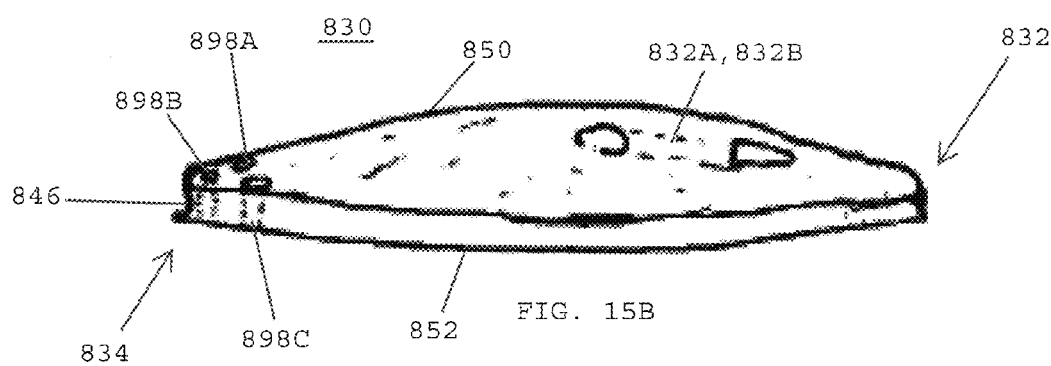
FIG. 15B shows a side elevational view of the hyoid extender shown in FIG. 15A.

Referring to FIGS. 15A and 15B, in one embodiment, a hyoid extender 830 desirably includes a plate having an anterior end 832 and a posterior end 834. The hyoid extender 830 preferably includes a top major surface 850 that extends between the anterior and posterior ends 832, 834 of the plate and an opposing bottom major surface 852 that also extends between the anterior and posterior ends 832, 834 of the plate. The top major surface 850 may have a slight convex curve extending between the anterior and posterior ends and the lateral sides of the anchoring element.

Referring to FIGS. 15A and 15B, the hyoid extender 830 desirably includes a pair of channels 832A, 832B that are formed adjacent the top major surface 850 of the anchoring element. Referring to FIG. 15A, the first channel 832A has a first opening 890 adjacent the anterior end 832 and a second opening 892 positioned between the first opening 890 and the posterior end 834 of the hyoid extender. The second channel 832B desirably includes a first opening 894 located adjacent the anterior end 832 and a second opening 896 located between the first opening 894 and the posterior end 834 of the hyoid extender. The first and second openings 890, 892 of the first channel 832A are desirably in communication with one another, and both of the first and second openings 890, 892 of the first channel 832A are desirably accessible at the top major surface 850 of the anchoring element. Similarly, the first and second openings 894, 896 of the second channel 832B are in communication with one another and are preferably accessible at the top major surface 850 of the anchoring element. The channels are adapted to receive at least a portion of the tongue suspension element for coupling the tongue suspension element and the hyoid extender together. In one embodiment, the first opening in the first or second channel is on top of the hyoid extender and the second opening on the first or second channel is on the bottom of the hyoid extender.

Referring to FIG. 15B, in one embodiment, at least one of the channels 832A, 832B extends at an oblique angle relative to the longitudinal axis of the anchoring element 830. Although the present invention is not limited by any particular theory of operation, it is believed that extending at least one of the channels at an oblique angle eliminates pinching or cutting of a tongue suspension element as it passes through one of the channels 832A, 832B.

Referring to FIGS. 15A and 15B, the posterior end 834 of the hyoid extender 830 desirably includes one or more through openings 898A-898C. The through openings 898A-898O are desirably used for securing (e.g. suturing) the posterior end 834 of the hyoid extender to a hyoid bone. Referring to FIG. 15B, in one embodiment, the posterior end 834 of the hyoid extender preferably includes a concave surface 846 adapted to engage and conform to a hyoid bone such as an anterior face of a hyoid bone.

Figure 16A:
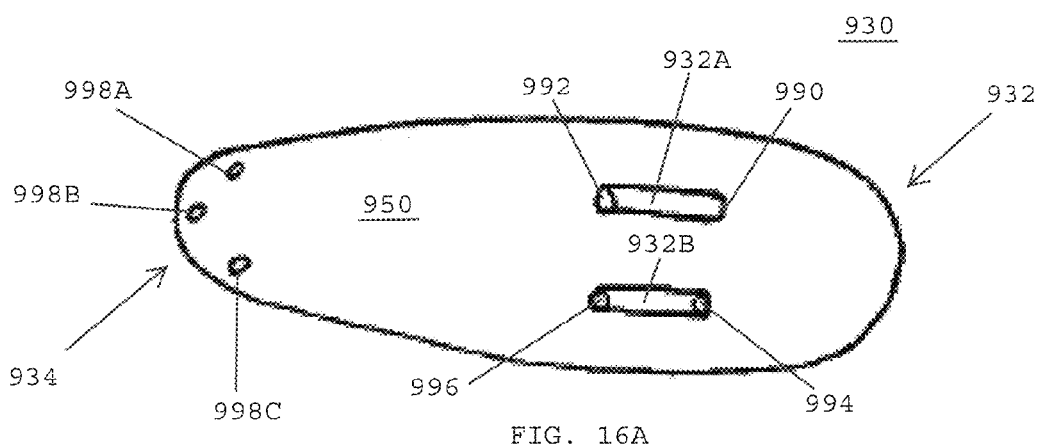
FIG. 16A shows a top plan view of a hyoid extender, in accordance with one embodiment of the present invention.
Figure 16B:
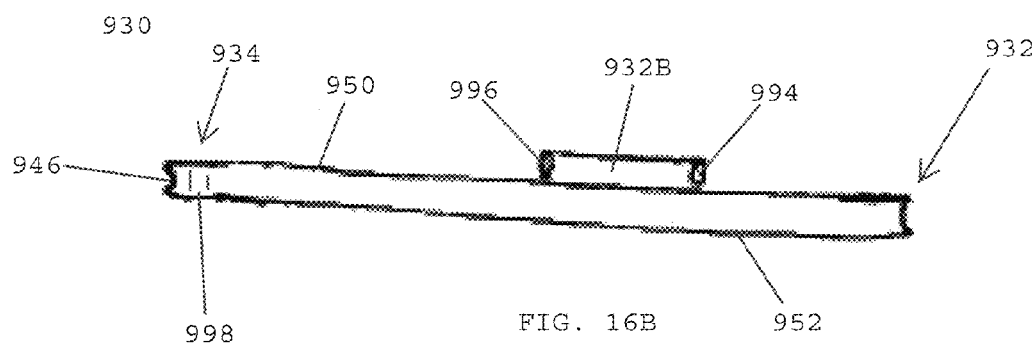
FIG. 16B shows a side view of the hyoid extender shown in FIG. 16A.

Referring to FIGS. 16A and 16B, in one embodiment, a hyoid extender 930 desirably includes an anterior end 932 and an opposite posterior end 934. The hyoid extender 930 desirably includes a top major surface 950 that extends between the anterior and posterior ends 932, 934 and an opposing bottom major surface 952 that also extends between the anterior and posterior ends. In one embodiment, the hyoid extender 930 is preferably shaped like an oval disc.

Referring to FIGS. 16A and 16B, the hyoid extender 930 desirably includes a pair of tubular-shaped elements 932A, 932B that overlie the top major surface 950 of the anchoring element. Referring to FIG. 16A, the first tubular element 932A has a first opening 990 adjacent the anterior end 932 of the hyoid extender and a second opening 992 positioned between the first opening 990 and the posterior end 934 of the hyoid extender. The second tubular element 932B desirably includes a first opening 994 located adjacent the anterior end 932 of the hyoid extender and a second opening 996 located between the first opening 994 and the posterior end 934. The first and second openings 990, 992 of the first tubular element 932A are desirably in communication with one another, and are desirably accessible at the top major surface 950 of the anchoring element. Similarly, the first and second openings 994, 996 of the second tubular element 932B are in communication with one another, and are accessible at the top major surface 950 of the anchoring element. In one embodiment, at least one of the first and second ends of a tongue suspension member may be passed through one of the first and second tubular elements 932A, 932B for securing the tongue suspension element to the hyoid extender.

Referring to FIG. 16B, in one embodiment, at least one of the tubular elements 932A, 932B may extend at an oblique angle relative to the top major surface 950 of the anchoring element 930. Although the present invention is not limited by any particular theory of operation, it is believed that the oblique angle eliminates pinching or cutting of the tongue suspension element as it passes through at least one of the tubular elements 932A, 932B.

Referring to FIGS. 16A and 16B, the posterior end 934 of the hyoid extender 930 desirably includes one or more through openings 998A-998C that extend between the first and second major faces 950, 952. The through openings 998A-998C are desirably used for securing the posterior end 934 of the hyoid extender to a hyoid bone. Referring to FIG. 16B, in one embodiment, the posterior end 934 of the hyoid extender includes a concave surface 946 adapted to engage and conform to an anterior face of a hyoid bone.

The embodiments shown in FIGS. 15A-15B and 16A-16B enable the ends of the tongue suspension element to engage the hyoid extender at one point and exit at another. In both embodiments, the hyoid extender is preferably monolithic, and may be manufactured by injection mold casting, or machining of a biocompatible polymer or metal. The hyoid extender is preferably made of non-resorbable biocompatible materials such as silicone, Teflon®, non-resorbable biocompatible polymers, and non-resorbable biocompatible metals. The openings for the loop are preferably oriented more towards the mandible side of the hyoid extender so as to provide a better angle for implantation and make access to the loops easier during implantation or adjustment. Holes may be placed at either end of the device, and preferably at least one hole is located on the posterior end (i.e. the hyoid side of the anchoring element) so as to allow for fixation to the hyoid bone by sutures, if necessary. In one embodiment, the posterior edge of the hyoid extender on the hyoid bone side may be chamfered to allow for a better fit against the hyoid bone when abutment occurs. In addition, the hyoid side of the hyoid extender may be thinner than the mandible side so as to not cause any irritation to closely packed muscles inserting on the hyoid bone. FIGS. 15A-15B show a hyoid extender having a dome-shaped top surface. FIGS. 16A-16B show a hyoid extender having two distinct tunnels projecting from the top surface thereof. In both embodiments, the channel or tunnel is preferably adapted for enabling the tongue suspension element to pass therethrough. The tongue suspension element may then be stapled or clamped together after each free end of the tongue suspension element passes through the tunnel.

Figure 17A:
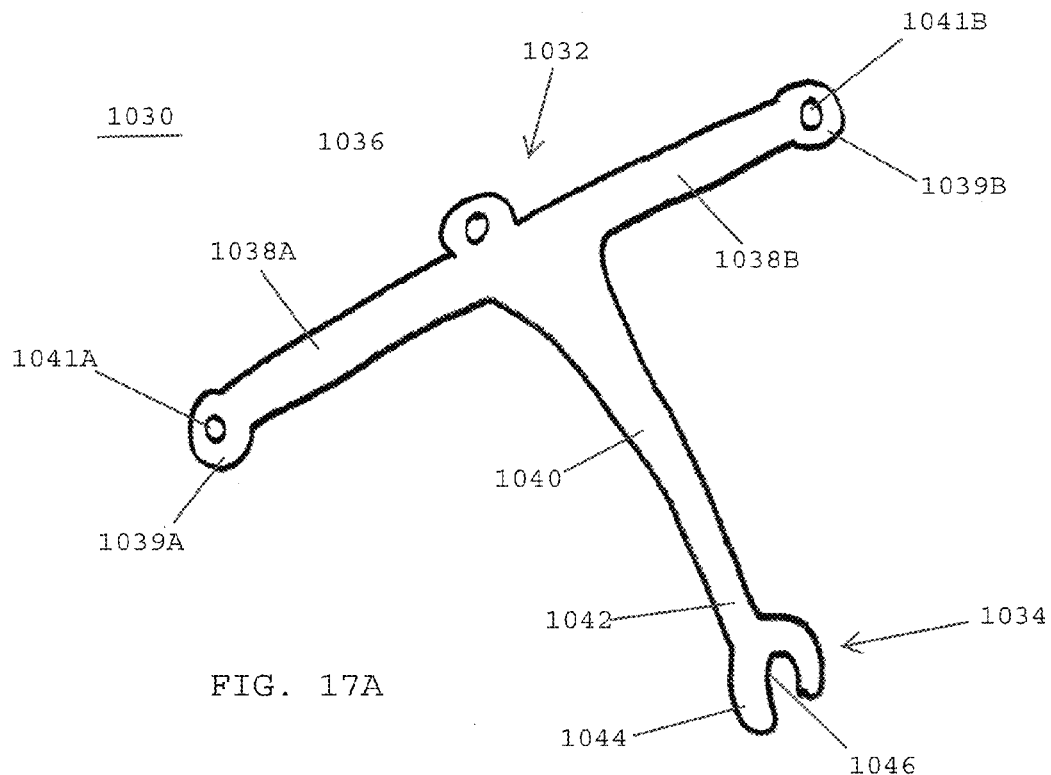
FIGS. 17A and 17B show a hyoid extender that is at least partially absorbable, in accordance with one embodiment of the present invention.

Referring to FIG. 17A, in accordance with one embodiment, a hyoid extender 1030 is at least partially absorbable so that after implantation at least a portion of the hyoid extender is reabsorbed within the body leaving one or more flexible connections as anchor points. Referring to FIG. 17A, the at least partially absorbable hyoid extender 1030 includes an anterior end 1032 and a posterior end 1034. The anterior end 1032 includes an anterior loop 1036 that is preferably adapted to be coupled with a tongue suspension element, as described above. The elongated shaft 1040 desirably includes an anchoring arm 1042 that extends to the posterior end 1034 of the hyoid extender 1030. The posterior end of the anchoring arm 1042 preferably includes a hyoid bone engaging element 1044 having a concave surface 1046 adapted to abut against and/or engage a hyoid bone. The at least partially absorbable hyoid extender 1030 also preferably includes an elongated shaft 1040 that extends between the anterior and posterior ends 1032, 1034 thereof.

Figure 17B:
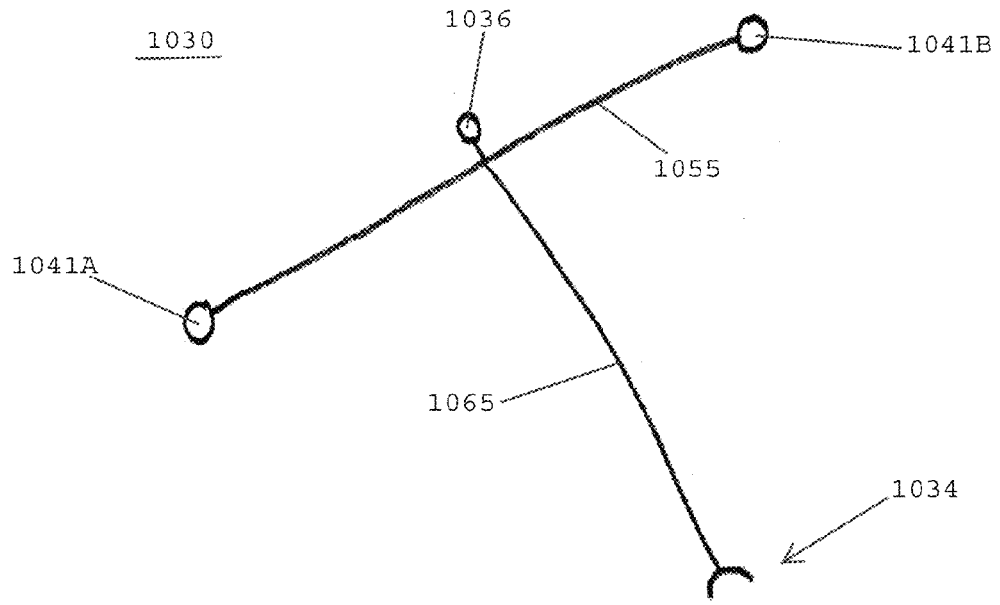

Referring to FIGS. 17A and 17B, in one embodiment, the hyoid extender 1030 includes a pair of opposing stabilizing arms 1038A, 1038B that preferably extend in lateral directions adjacent the anterior end 1032 of the hyoid extender 1030. The outer ends of the stabilizing arms 1038A, 1038B desirably include respective tissue anchoring loops 1039A, 1039B that define openings 1041A, 1041B. Upon implantation, tissue may grow through the openings 1041A, 1041B. After a period of time, at least a portion of the hyoid extender 1030 may be absorbed by the body leaving behind a first flexible connection 1055 extending laterally between the openings 1041A, 1041B, and a second flexible connection 1065 extending between the anterior loop 1036 anchored to the tongue suspension element and the posterior end 1034 of the hyoid bone extender. Although the embodiment shown in FIGS. 17A and 17B is not limited by any particular theory of operation, it is believed that providing an at least partially absorbable hyoid bone extender provides long term lateral stabilization in the absence of a rigid structure, thereby improving long-term comfort and patient compliance. If necessary after implantation, a surgeon may later remove the hyoid bone extender 1030 by cutting the laterally extending flexible connection 1055 adjacent the openings 1041A, 1041B so that the cut away portion may be removed. Similarly, the longitudinal flexible connection 1056 may be also removed by cutting the member adjacent the anterior loop 1036 and/or the posterior end 1034.

Figure 18A:
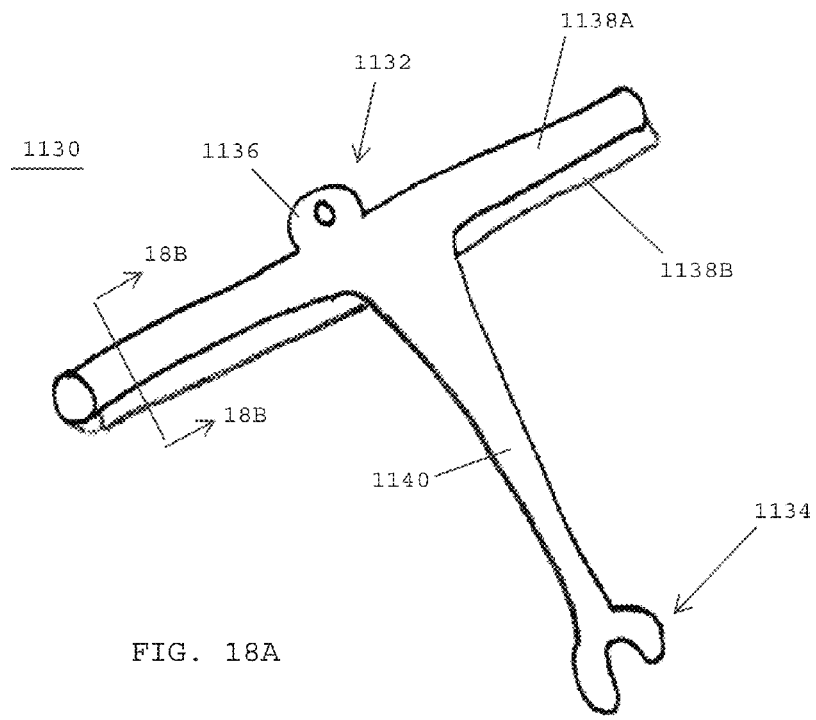
FIGS. 18A and 18B show a hyoid extender having a pair of vertically spaced stabilizing arms, in accordance with one embodiment of the present invention.
Figure 18B:
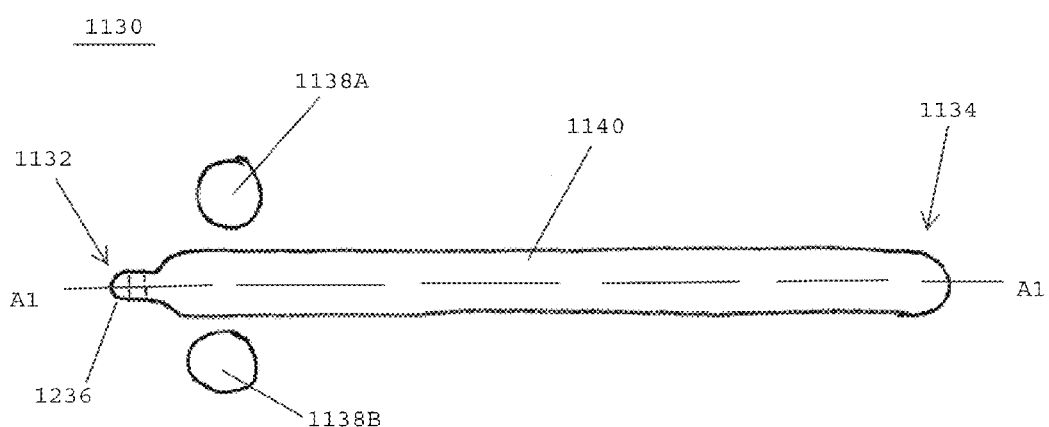

Referring to FIGS. 18A and 18B, in one embodiment, a hyoid extender 1130 includes an anterior end 1132, a posterior end 1134, and an anterior loop 1136 adjacent the anterior end adapted to be coupled with a tongue suspension element. The hyoid extender 1130 preferably includes an elongated shaft 1140 that extends between the anterior and posterior ends thereof. The hyoid extender 1130 preferably includes a first stabilizing bar 1138A that extends laterally from both sides of the elongated shaft 1140 and a second stabilizing bar 1138B that also preferably extends from both sides of the elongated shaft 1140. Referring to FIG. 18B, the first and second stabilizing arms are vertically spaced from one another so that the first stabilizing bar 1138A lies above the longitudinal axis $A_1$ of the elongated shaft 1140 and the second stabilizing arm 1138B extending below the longitudinal axis of the elongated shaft 1140. The vertical spacing between the stabilizing arms 1138A, 1138B enable the arms to be placed both above and below a set of muscles, such as the geniohyoid or digastrics, to provide vertical stability, which enables the paired muscles to be captured from three sides.

In one embodiment, a lubricious coating may be placed over an outer surface of a hyoid extender so as to reduce drag of sliding musculature against either the elongated shaft of the hyoid extender or the laterally extending stabilizing arms. In one embodiment, the lubricious coating may include a hydrophilic material such as those utilized on catheters.

In one embodiment, the tongue suspension element and/or the hyoid extender may have a coating, such as silicone that is provided over non-woven or woven fabric so as to provide flexible implants that are impervious to in-growth but that remain compliant over time. In one embodiment, the non-woven or woven fabric may be welded to itself or formed to provide axial resistance to buckling, to provide directional support that resists kinking, or to prevent collapse, while providing larger flexible surface areas between the musculature to prevent twisting.

The non-absorbable materials of the implant disclosed herein may include polymeric materials such as non-resorbable polymers, silicone, polyethylene terephalate, polytetrafluoroethylene, polycarbonate, polyurethane and polypropylene, nitinol, stainless steel, and/or composite materials.

In one embodiment of the present invention, a system for treating OSA includes an elongated element that is wrapped around fibers such as muscle fibers extending through a tongue. In one embodiment, some of the fibers are preferably intrinsic muscle fibers that extend in a generally vertical direction though the tongue, such as the intrinsic verticalis muscle fibers. As used in this embodiment, the term "vertical" describes a direction relative to upper and lower ends of a human body. The elongated element is preferably looped around the muscle fibers at least once so as to capture the muscle fibers within the loop. The looped elongated element may extend in a substantially horizontal plane relative to the vertically extending fibers. After a bundle of muscle fibers have been captured within the looped elongated element, the muscle fibers are desirably compacted or compressed together by the elongated element. In one embodiment, tension may be applied to a free end of the elongated element for moving the tongue away from an opposing pharyngeal wall. The free end of the elongated element may be anchored to a hyoid extender implanted in inframandibular musculature for maintaining the tongue in a forward shifted position so that the back of the tongue does not collapse against the opposing pharyngeal wall during sleep.

Although the above-described embodiments are not limited by any particular theory of operation, it is recognized that some of the intrinsic muscle fibers in the tongue, such as the intrinsic verticalis muscles, extend in a generally vertical direction as they terminate near the superior mucosal surface of the tongue. As such, a horizontally-extending band or loop may be secured around a bundle of these vertically-extending fibers and the band or loop may be pulled in an anterior and/or inferior direction for shifting the position of the tongue. A tether or elongated element may also be coupled with the band or loop, with a lower end of the tether or elongated element anchored in inframandibular musculature to maintain the tongue in a forward shifted position so that the back of the tongue remains spaced from an opposing pharyngeal wall.

The present invention provides a number of advantages over prior art systems, devices, and methods for treating obstructive sleep apnea syndrome and hypopnea. First, the systems, devices and methods disclosed herein provide for simple surgical procedures that are minimally invasive. Typically, the systems, devices, and methods disclosed herein may be utilized during an outpatient procedure. In addition, the systems, devices, and methods disclosed herein provide both immediate and long term results for treating obstructive sleep apnea syndrome and hypopnea. Moreover, the systems, devices, and methods disclosed herein do not require a significant level of patient compliance.

In addition, the present invention does not anchor the posterior aspect of the tongue to a fixed hard structure, such as the mandible and is only preferably fixated within and or against soft or moveable tissues. Thus, the present invention is significantly less likely to affect swallowing or speech, thereby providing a great improvement over prior art devices, systems and methods. The present invention also preferably uses materials having long-term biocompatibility.

Although various embodiments disclosed herein relate to use in humans, it is contemplated that the present invention may be used in mammals, and in animals having air passages. Moreover, the systems, devices, and methods disclosed herein may incorporate any materials that are biocompatible, as well as any solutions or components that minimize rejection, and improve acceptance of the device by a body after the device has been implanted.

The present application may incorporate one or more of the features disclosed in commonly assigned U.S. patent application Ser. No. 12/182,402, filed Jul. 30, 2008; Ser. No. 12/183,955, filed Jul. 31, 2008; Ser. No. 12/257,563, filed Oct. 24, 2008; Ser. No. 12/261,102, filed Oct. 30, 2008; and Ser. No. 12/325,350, filed Dec. 1, 2008; and U.S. Patent Appln. Pub. Nos. 2007/0005109 and 2007/0005110, the disclosures of which are hereby incorporated by reference herein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A system for treating obstructive sleep apnea comprising:
   a first implantable element having a first free end, a second free end, and a center section located between said first and second free ends, said center section being implanted in a tongue and said first and second free ends extending beneath the tongue into inframandibular musculature;
   a second implantable element having an anterior end, a posterior end, an anchor point located at the anterior end, first and second laterally extending stabilizing arms adjacent the anterior end and posterior to said anchor point, an elongated shaft posterior to said first and second stabilizing arms and extending toward the posterior end of said second implantable element, wherein said elongated shaft is split adjacent the posterior end of said second implantable element into a first arm having a posterior end including a first hyoid bone engaging element having a first concave surface and a second arm having a posterior end including a second hyoid bone engaging element having a second concave surface, wherein said second implantable element is implanted in inframandibular musculature with said anchor point located nearer an anterior end of said inframandibular musculature, and said first and second concave surfaces located nearer a posterior end of said inframandibular musculature and engaging an anterior surface of a hyoid bone, said elongated shaft extending posteriorly from said anchor point, and said elongated shaft extending between muscle planes in the inframandibular musculature, wherein said first and second free ends of said first implantable element are attached to said anchor point at the anterior end of said second implantable element.

2. The system as claimed in claim 1, wherein said first and second implantable elements have outer surfaces that are impermeable to tissue in-growth.

3. The system as claimed in claim 1, wherein said first and second implantable elements are biocompatible and non-resorbable.

4. The system as claimed in claim 1, wherein said first implantable element comprises materials selected from the group consisting polytetrafluoroethylene, polyurethane, polyethylene, teraphthalate, polypropylene, and silicone.

5. The system as claimed in claim 1, wherein said second implantable element comprises materials selected from the group consisting of e-PTFE, polypropylene, silicone, polyurethane, nitinol, stainless steel, polyethylene terepthalate, and silk.

6. The system as claimed in claim 1, wherein said first implantable element is elongated and comprises:
a lower end including said first free end, and said second free end, and an upper end including said center section located between said first and second free ends, wherein said first implantable element has a length and a cross sectional area that remains constant along the length.

7. The system as claimed in claim 6, wherein said center section includes a buttress defining a larger width region of said first implantable element.

8. The system as claimed in claim 7, wherein with the upper end of said first implantable element implanted in the tongue, said buttress extends along an axis that traverses an anterior-posterior axis of the tongue.

9. The system as claimed in claim 6, wherein the at least one anchor point comprises a loop located at the anterior end of said second implantable element that is adapted to receive said first and second free ends of said first implantable element.

10. The system as claimed in claim 1, wherein said first implantable element comprises an elongated, flexible ribbon or an elongated suture.

11. The system as claimed in claim 9, wherein said first and second laterally extending stabilizing arms extend between the muscle planes located in the inframandibular musculature.

12. The system as claimed in claim 1, wherein said concave surface engages the anterior surface of the hyoid bone.

13. The system as claimed in claim 12, wherein said first and second concave surfaces are spaced away from one another at the posterior end of said second implantable element and said first and second concave surfaces face toward the posterior end of said second implantable element and face away from the anterior end of said second implantable element.

14. A system for treating obstructive sleep apnea comprising:
a first element having a first free end, a second free end, and a center section located between said first and second free ends, said center section being implanted in a tongue and said first and second free ends extending beneath the tongue into inframandibular musculature; and
a second element implanted between muscle planes in the inframandibular musculature located beneath the tongue, said second element having an anterior end coupled with said first and second free ends of said first element, a posterior end, an anchor point located at the anterior end, first and second laterally extending stabilizing arms adjacent the anterior end and posterior to said anchor point, an elongated shaft posterior to said first and second stabilizing arms and extending toward the posterior end of said second element, wherein said elongated shaft is split at the posterior end of said second element into a first arm having a posterior end including a first hyoid bone engaging element having a first concave surface and a second arm having a posterior end including a second hyoid bone engaging element having a second concave surface, wherein said second element is implanted in inframandibular musculature with said anchor point located nearer an anterior end of said inframandibular musculature, said first and second concave surfaces located nearer a posterior end of said inframandibular musculature, said first and second concave surfaces engaging a hyoid bone, and said elongated shaft extending between the muscle planes in the inframandibular musculature and extending posteriorly from said anchor point to said first and second concave surfaces, wherein said first and second free ends of said first element are attached to said anchor point at the anterior end of said second element.

15. The system as claimed in claim 14, wherein an upper end of said first element comprises at least one loop implanted in the tongue and a lower end of said first element comprises said first and second free ends disposed in the inframandibular musculature for anchoring said first element with said second element.

16. The system as claimed in claim 15, wherein said concave surface at the posterior end of said second element engages an anterior face of the hyoid bone.

17. A method for treating obstructive sleep apnea comprising:
providing a tongue suspension element having a center section and two free ends;
implanting the center section of said tongue suspension element in a tongue;
advancing the two free ends of said tongue suspension element beneath the tongue and into inframandibular musculature;
positioning the two free ends of said tongue suspension element in the inframandibular musculature located beneath the tongue;
providing a hyoid bone extender having an anterior end, a posterior end, an anchor point located at said anterior end, first and second laterally extending stabilizing arms adjacent said anterior end and posterior to said anchor point, an elongated shaft posterior to said first and second stabilizing arms and extending toward said posterior end of said hyoid bone extender, wherein said elongated shaft adjacent the posterior end of said hyoid bone extender is split into a first arm having a posterior end including a first hyoid bone engaging element having a first concave surface and a second arm having a posterior end including a second hyoid bone engaging element having a second concave surface;

implanting said hyoid bone extender between muscle planes in the inframandibular musculature located beneath the tongue so that said anchor point is located nearer an anterior end of said inframandibular musculature, said first and second concave surfaces are located nearer a posterior end of said inframandibular musculature, and said elongated shaft extends posteriorly from said anterior end of said hyoid bone extender;

anchoring the two free ends of said tongue suspension element positioned within the inframandibular musculature to said anchoring point at said anterior end of said hyoid bone extender; and coupling said first and second concave surfaces at the posterior ends of said first and second split arms with a hyoid bone for moving a posterior surface of the tongue away from an opposing surface of a pharyngeal wall.

18. The method as claimed in claim 17, wherein the method further comprises abutting said first and second concave surfaces at said posterior ends of said first and second split arms against an anterior surface of the hyoid bone.

19. The method as claimed in claim 17, further comprising using sutures, clips, clamps, staples, barbs, or adhesive for anchoring said first and second concave surfaces of said hyoid bone extender to the hyoid bone.

20. The system as claimed in claim 1, wherein said first and second hyoid bone abutting elements at said posterior ends of said first and second split arms define the posteriormost end of said second implantable element.

21. The system as claimed in claim 1, wherein said first and second laterally extending stabilizing arms extend away from one another along respective axes that define a first angle and said first and second split arms extend away from one another along respective axes that define a second angle that is smaller than the first angle.

22. The system as claimed in claim 14, wherein said first and second hyoid bone abutting elements at said posterior ends of said first and second split arms define the posteriormost end of said second implantable element.

23. The system as claimed in claim 14, wherein said first and second laterally extending stabilizing arms define a first angle and said first and second split arms define a second angle that is smaller than the first angle.

24. The method as claimed in claim 17, wherein said first and second hyoid bone abutting elements at said posterior ends of said first and second split arms define the posteriormost end of said second implantable element.

25. The method as claimed in claim 17, wherein said first and second laterally extending stabilizing arms extend away from one another along respective axes that define a first angle and said first and second split arms extend away from one another along respective axes that define a second angle that is smaller than the first angle.

* * * * *